United States Patent
Uemori et al.

(10) Patent No.: US 7,422,888 B2
(45) Date of Patent: Sep. 9, 2008

(54) THERMOTOLERANT RIBONUCLEASE H

(75) Inventors: Takashi Uemori, Shiga (JP); Yoshimi Sato, Shiga (JP); Nobuto Koyama, Kyoto (JP); Ryo Hirano, Shiga (JP); Hikaru Takakura, Shiga (JP); Hiroshi Kobori, Shiga (JP); Yuji Hashimoto, Shiga (JP); Kiyozo Asada, Shiga (JP); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 116 days.

(21) Appl. No.: 10/380,430

(22) PCT Filed: Sep. 13, 2001

(86) PCT No.: PCT/JP01/07930

§ 371 (c)(1),
(2), (4) Date: Mar. 14, 2003

(87) PCT Pub. No.: WO02/22831

PCT Pub. Date: Mar. 21, 2002

(65) Prior Publication Data

US 2004/0038366 A1    Feb. 26, 2004

(30) Foreign Application Priority Data

Sep. 14, 2000 (JP) .............................. 2000-280785
Mar. 7, 2001 (JP) .............................. 2001-064074

(51) Int. Cl.
*C12N 9/22* (2006.01)
*C12N 9/14* (2006.01)
*C07H 21/04* (2006.01)

(52) U.S. Cl. ...................... 435/199; 435/195; 536/23.1; 536/23.2

(58) Field of Classification Search ................... 435/197
See application file for complete search history.

(56) References Cited

U.S. PATENT DOCUMENTS 5,610,066 A    3/1997 Fuller et al.

FOREIGN PATENT DOCUMENTS

JP    2533671    6/1996
JP    11-32772   2/1999

OTHER PUBLICATIONS

Itaya et al Molecular cloning of a ribonuclease H (RNase HI) gene from an extreme thermophile Thermus thermophilus HB8: a thermostable RNase H can functionally replace the *Escherichia coli* enzyme in vivo. Nucleic Acids Res. Aug. 25, 1991;19(16):4443-9.*
Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Klenk et al., SwissProt, Accession O29634, Gene AF0621.
Klenk et al., Genbank, Accession AE 001062.
Kawarabayasi et al., "Complete Sequence and Gene Organization of the Genome of a Hyper-Thermophilic Archaebacterium, *Pyrococcus horikoshii* OT3", *DNA Research*, vol. 5, pp. 55-76 (1998).
Kawarabayasi et al., SwissProt, Accession O59351, Gene PH1650.
Kawarabayasi et al., EMBL, Accession AP000006.
Nelson et al., "Evidence for Lateral Gene Transfer Between Archaea and Bacteria from Genome Sequence of *Thermotoga maritima*", *Nature*, vol. 399, No. 6734, pp. 323-329 (May 27, 1999).
Nelson et al., SwissProt, Accession Q9X017, Gene TM0915.
Nelson et al., Genbank, Accession AE001755.
Haruki et al., "Gene Cloning and Characterization of Recombinant RNase HII from a Hyperthermophilic Archaeon", *Journal of Bacteriology*, vol. 180, No. 23, pp. 6207-6214 (Dec. 1998).
Klenk et al., "The Complete Genome Sequence of the Hyperthermophilic, Sulphate-Reducing Archaeon *Archaeoglobus fulgidus*", *Nature*, vol. 390, No. 6665, pp. 364-370 (Nov. 27, 1997).
Kanaya et al., "Overproduction and Preliminary Crystallographic Study of Ribonuclease H from *Escherichia coli*", *The Journal of Biological Chemistry*, vol. 264, No. 20, pp. 11546-11549 (Jul. 15, 1989).
Wang et al., "Site-Specific Mutagenesis of the Human Interleukin-2 Gene: Structure-Function Analysis of the Cysteine Residues", *Science*, vol. 224, pp. 1431-1433 (Jun. 29, 1984).
Brown et al., "Cultivation Techniques for Hyperthermophilic Archaebacteria: Continuous Culture of *Pyrococcus furiosus* at Temperatures Near 100° C.", *Applied and Environmental Microbiology*, vol. 55, No. 8, pp. 2086-2088 (Aug. 1989).
Ohtani et al., "Identification of the Genes Encoding $Mn^{2+}$-Dependent RNase HII and $Mg^{2+}$-Dependent RNase HIII from *Bacillus subtilis*: Classification of RNases H into Three Families", *Biochemistry*, vol. 38, pp. 605-618 (1999).
Pearson et al., "Improved Tools for Biological Sequence Comparison", *Proc. Natl. Acad. Sci.*, vol. 85, pp. 2444-2448 (Apr. 1988).
Database UniProt accession No. 029634.
Database UniProt accession No. 074035.
Database UniProt accession No. AAW97111.
Database EMBL accession No. AAX15332.
Database EMBL accession No. AB012613.
Database UniProt accession No. E71146.
Database UniProt accession No. E71145.
NCBI GenBank sequence database Accession No. AAB90620.
NCBI GenBank sequence database Accession No. AAD35996.

* cited by examiner

*Primary Examiner*—Richard G Hutson
(74) *Attorney, Agent, or Firm*—Browdy and Neimark, PLLC

(57) ABSTRACT

Polypeptides having an RNase H activity highly useful in genetic engineering; genes encoding these polypeptides; and a process for genetic engineeringly producing these polypeptides.

2 Claims, No Drawings

THERMOTOLERANT RIBONUCLEASE H

TECHNICAL FIELD

The present invention relates to a polypeptide, specifically a polypeptide having a ribonuclease H activity which is highly valuable for genetic engineering. The present invention also relates to a gene that is useful for producing said polypeptide by genetic engineering. The present invention further relates to a method for producing said polypeptide by genetic engineering.

BACKGROUND ART

There are endo-type and exo-type ribonucleases (RNA-degrading enzymes). Their substrate specificities are various, and they are involved in complicated physiological activities. Enzymes such as ribonuclease $T_1$, ribonuclease $T_2$, ribonuclease H, ribonuclease P, ribonuclease I, ribonuclease II, ribonuclease III, ribonuclease IV, ribonuclease L are known to have ribonuclease activities.

Ribonuclease H (hereinafter also referred to as RNase H) was first isolated from calf thymus by W. H. Stein and P. Hausen in 1969. RNase Hs are currently classified into cellular RNase Hs and viral RNase Hs. The cellular RNase Hs are widely present in eukaryotes such as various animal cells and yeasts and prokaryotes such as *Escherichia coli*, whereas the viral RNase Hs are present in RNA tumor viruses. Several kinds of RNase H activities are present in a cell. They require divalent metal ions such as $Mg^{2+}$ and $Mn^{2+}$.

An RNase H from *Escherichia coli* is a hydrolase that consists of 155 amino acids, has a molecular weight of about 17 kDa and has a substrate specificity of specifically cleaving only the RNA strand in a DNA-RNA hybrid in an endo-type manner. The resulting oligomer has a phosphate group at the 5' end and a hydroxyl group at the 3' end.

RNase HI and RNase HII have been identified as RNase Hs from *E. coli*. It has been shown that RNase HI has the following physiological functions in the replication of the Col E1 plasmid: 1) it degrades RNAs bound to portions other than the normal replication origin to ensure the normal replication origin; and 2) it synthesizes an RNA primer specific for the normal replication origin. The function of RNase HII remains unknown.

It is considered that RNase H increasingly becomes important with the development of genetic engineering. However, the expression level of this enzyme in *E. coli* is quite low. Then, production of this enzyme using recombinant DNA techniques has been attempted. RNase Hs produced using recombinant DNA techniques are now supplied from BRL, Amersham Pharmacia Biotech, Takara Shuzo and the like.

These commercially available recombinant RNase Hs are produced using *Escherichia coli* as a host (Kanaya et al., The Journal of Biological Chemistry, 264:11546-11549 (1989)). A method of producing an RNase H from a thermophile, which is much more stable than RNase H from *E. coli*, using *E. coli* has been reported (Kanaya et al., Dai 2 Kai Nippon Tanpakukougakukai Nenkai Program/Abstract (1990) pp. 69; Japanese Patent No. 2533671). However, the enzymatic activity of the RNase H from a thermophile produced using *E. coli* was lower than that of RNase H from *E. coli*.

RHase Hs have uses as exemplified below based on the substrate specificities, and attention is paid to RNase Hs as very valuable enzymes:

1) removal of template mRNA upon cDNA cloning;
2) removal of poly(A) region in mRNA; and
3) fragmentation of RNA.

However, as described above, only thermostable RNase Hs of which the productivities and the enzymatic activities are lower than those of RNase H from *E. coli* are available. Thus, development of a thermostable RNase H of which the productivity and the enzymatic activity are equivalent to or more than those of the RNase H from *E. coli* has been desired for expanding the uses of RNase H.

OBJECTS OF INVENTION

The main object of the present invention is to provide a polypeptide having an RNase H activity which is highly valuable for genetic engineering, a gene encoding said polypeptide and a method for producing said polypeptide by genetic engineering.

SUMMARY OF INVENTION

In view of the circumstances as described above, the present inventors have studied intensively and conducted screening in order to obtain a thermostable RNase H. As a result, the present inventors have found a thermostable RNase H polypeptide having a high RNase H activity. Furthermore, the present inventors have found that the productivity of the thus obtained thermostable RNase H in production using genetic engineering techniques is high. Thus, the present invention has been completed.

The present invention is outlines as follows. The first aspect of the present invention relates to a thermostable ribonuclease H polypeptide, i.e., a polypeptide having a thermostable ribonuclease H activity, which is selected from the group consisting of:

(a) a polypeptide having the amino acid sequence of SEQ ID NO:9, 17, 23, 32, 37, 47, 57 or 59, or a portion thereof;

(b) a polypeptide having an amino acid sequence in which at least one amino acid residue is deleted, added, inserted or substituted in the amino acid sequence of SEQ ID NO:9, 17, 23, 32, 37, 47, 57 or 59; and (c) a polypeptide having an amino acid sequence that shares at least 71% homology with the amino acid sequence of SEQ ID NO:9, 17, 23, 32, 37, 47, 57 or 59.

The second aspect of the present invention relates to a nucleic acid encoding a thermostable ribonuclease H, i.e., a nucleic acid encoding a polypeptide having a thermostable ribonuclease H activity, which is selected from the group consisting of:

(a) a nucleic acid encoding a polypeptide having the amino acid sequence of SEQ ID NO:9, 17, 23, 32, 37, 47, 57 or 59, or a portion thereof;

(b) a nucleic acid encoding a polypeptide having an amino acid sequence in which at least one amino acid residue is deleted, added, inserted or substituted in the amino acid sequence of SEQ ID NO:9, 17, 23, 32, 37, 47, 57 or 59;

(c) a nucleic acid having the nucleotide sequence of SEQ ID NO:8, 16, 22, 31, 36, 46, 56 or 58;

(d) a nucleic acid in which at least one nucleotide is deleted, added, inserted or substituted in the nucleotide sequence of SEQ ID NO:8, 16, 22, 31, 36, 46, 56 or 58 such that the deletion, addition, insertion or substitution of the nucleotide results in translation into an amino acid sequence;

(e) a nucleic acid that is hybridizable to any one of the nucleic acids of (a) to (d) or complementary strands thereof under stringent conditions; and (f) a nucleic acid having a nucleotide sequence that shares at least 69% homology with the nucleotide sequence of SEQ ID NO:8, 16, 22, 31, 36, 46, 56 or 58.

The third aspect of the present invention relates to a recombinant DNA comprising the nucleic acid of the second aspect.

The fourth aspect of the present invention relates to a transformant transformed with the recombinant DNA of the third aspect.

The fifth aspect of the present invention relates to a method for producing a polypeptide having a thermostable ribonuclease H activity, the method comprising:

culturing the transformant of the fourth aspect; and collecting a polypeptide having a thermostable ribonuclease H activity from the culture.

The sixth aspect of the present invention relates to a polypeptide having a thermostable ribonuclease H activity, which is obtainable by culturing a transformant into which any one of the plasmids pRHB11, pBCA3Nd2, pPFU220, pTM-RNH, pPHO238, pAFU204, pTLI204 and pTCE207 is transferred. *Escherichia coli* strains harboring these plasmids are deposited under Budapest Treaty at International Patent Organism Depositary, National Institute of Advanced Industrial Science and Technology under accession numbers FERM BP-7655, FERM BP-7653, FERM BP-7654, FERM BP-7652, FERM BP-7692, FERM BP-7691, FERM BP-7693 and FERM BP-7694, respectively.

DETAILED DESCRIPTION OF THE INVENTION

Hereinafter, the present invention will be described in detail.

As used herein, an RNase H refers to a hydrolase that has a substrate specificity of specifically cleaving only the RNA strand in a DNA-RNA hybrid in an endo-type manner, wherein the resulting oligomer has a phosphate group at the 5' end and a hydroxyl group at the 3' end.

Although it is not intended to limit the present invention, having a thermostable RNase H activity as used herein with respect to a polypeptide means that the polypeptide has an RNase H activity after incubating it at a temperature of 60° C. or above for 15 minutes.

For example, a thermostable RNase H activity can be determined as follows.

1 mg of poly(rA) or poly(dT) (both from Amersham Pharmacia Biotech) is dissolved in 1 ml of 40 mM tris-HCl (pH 7.7) containing 1 mM EDTA to prepare a poly(rA) solution and a poly(dT) solution.

The poly(rA) solution (to a final concentration of 20 μg/ml) and the poly(dT) solution (to a final concentration of 30 μg/ml) are then added to 40 mM tris-HCl (pH 7.7) containing 4 mM $MgCl_2$, 1 mM DTT, 0.003% BSA and 4% glycerol. The mixture is reacted at 37° C. for 10 minutes and then cooled to 4° C. at prepare a poly(rA)-poly(dT) solution.

1 μl of an enzyme solution is added to 100 μl of the poly (rA)-poly(dT) solution. The mixture is reacted at 40° C. for 10 minutes. 10 pl of 0.5 M EDTA is added thereto to terminate the reaction. Absorbance at 260 nm is then measured. As a control, 10 μl of 0.5 M EDTA is added to the reaction mixture, the resulting mixture is reacted at 40° C. for 10 minutes, and the absorbance is then measured. A value (difference in absorbance) is obtained by subtracting the absorbance for the control from the absorbance for the reaction in the absence of EDTA. Thus, the concentration of nucleotide released from poly(rA)-poly(dT) hybrid by the enzymatic reaction is determined on the basis of the difference in absorbance. Thus, the thermostable RNase H activity according to the present invention can be determined.

Alternatively, the thermostable RNase H activity according to the present invention can be determined as follows. 100 μl of a reaction mixture [20 mM HEPES-potassium hydroxide (pH 8.5), 0.01% bovine serum albumin (Takara Shuzo), 1% dimethyl sulfoxide, 4 mM magnesium acetate, 20 μg/ml poly(dT) (Amersham Pharmacia Biotech), 30 μg/ml poly(rA) (Amersham Pharmacia Biotech)] which has been incubated at 40° C. is added to 1 μl of an enzyme solution of which the activity is to be determined. The mixture is reacted at 40° C. for 10 minutes. The reaction is then terminated by adding 10 μl of 0.5 M EDTA (pH 8.0). Absorbance at 260 nm is then measured.

One unit of an RNase H is defined as an amount of enzyme that increases $A_{260}$ corresponding to release of 1 nmol of ribonucleotide in 10 minutes calculated according to the following equation:

Unit=[Difference in Absorbance×Reaction Volume (ml)]/0.0152

The polypeptides of the present invention include a polypeptide having an amino acid sequence in which at least one amino acid residue is deleted, added, inserted or substituted in the amino acid sequence of SEQ ID NO:9, 17, 23, 32, 37, 47, 57 or 59 as long as it exhibits a thermostable RNase H activity.

A mutation such as deletion, insertion, addition or substitution of an amino acid in an amino acid sequence may be generated in a naturally occurring polypeptide. Such mutation may be generated due to a polymorphism or a mutation of the DNA encoding the polypeptide, or due to a modification of the polypeptide in vivo or during purification after synthesis. However, it is known that such a mutated polypeptide may exhibit a physiological or biological activity substantially equivalent to that of a polypeptide without a mutation if such a mutation is present in a portion that is not important for the retention of the activity or the structure of the polypeptide.

This is applicable to a polypeptide in which such a mutation is artificially introduced into an amino acid sequence of a polypeptide. In this case, it is possible to generate more various mutations. For example, it is known that a polypeptide in which a cysteine residue in the amino acid sequence of human interleukin-2 (IL-2) is replaced by a serine retains the interleukin-2 activity (Science, 224:1431 (1984)).

Furthermore, it is known that certain polypeptides have peptide regions that are not indispensable to their activities. Such peptide regions are exemplified by a signal peptide in a polypeptide to be secreted extracellularly, or a prosequence or pre-prosequence found in a precursor of a protease. Most of such regions are removed after translation or upon conversion into an active polypeptide. Such a polypeptide has a primary structure different from that of a polypeptide without the region to be removed, but finally exhibits an equivalent function.

Genes having nucleotide sequences of SEQ ID NOS:8, 16, 22, 31, 36, 46, 56 or 58 which are isolated according to the present invention encode polypeptides having the amino acid sequences of SEQ ID NOS:9, 17, 23, 32, 37, 47, 57 or 59, respectively. These polypeptides have thermostable RNase H activities. The polypeptides of the present invention include polypeptides from which peptide regions that are not indispensable to their activities have been deleted therefrom.

When a polypeptide is produced by genetic engineering, a peptide chain that is irrelevant to the activity of the polypeptide of interest may be added at the amino terminus or the carboxyl terminus of the polypeptide. For example, a fusion polypeptide, in which a portion of an amino terminus region of a polypeptide that is expressed at a high level in the host to be used is added at the amino terminus of the polypeptide of interest, may be prepared in order to increase the expression level of the polypeptide of interest. In another case, a peptide having an affinity for a specific substance may be added at the amino terminus or the carboxyl terminus of the polypeptide of interest in order to facilitate the purification of the expressed polypeptide. The added peptide may remain added if it does not have a harmful influence on the activity of the polypeptide of interest. If necessary, it may be engineered such that it can be removed from the polypeptide of interest by appropriate treatment, for example, by limited digestion with a protease.

Thus, a polypeptide having an amino acid sequence in which at least one amino acid residue is deleted, inserted, added or substituted in the amino acid sequence of SEQ ID NO:9, 17, 23, 32, 37, 47, 57 or 59 disclosed herein is encompassed by the present invention if it has a thermostable RNase H activity.

Furthermore, a polypeptide having an amino acid sequence that shares at least 71%, preferably 80%, more preferably 90% homology with the amino acid sequence of SEQ ID NO:9, 17, 23, 32, 37, 47, 57 or 59 disclosed herein is encompassed by the present invention if it has a thermostable RNase H activity.

The homology can be determined using, for example, a computer program DNASIS-Mac (Takara Shuzo), a computer algorithm FASTA (version 3.0; Pearson, W. R. et al., Pro. Natl. Acad. Sci., 85:2444-2448, 1988) or a computer algorithm BLAST (version 2.0, Altschul et al., Nucleic Acids Res. 25:3389-3402, 1997).

For example, a polypeptide that shares at least 44% homology with the amino acid sequence of the ribonuclease HII from *Bacillus caldotenax* (SEQ ID NO:9), at least 47% homology with the amino acid sequence of the ribonuclease HIII from *Bacillus caldotenax* (SEQ ID NO:17), at least 69% homology with the amino acid sequence of the ribonuclease H from *Pyrococcus furiosus* (SEQ ID NO:23), at least 53% homology with the amino acid sequence of the ribonuclease H from *Thermotoga maritima* (SEQ ID NO:59), at least 51% homology with the amino acid sequence of the ribonuclease H from *Archaeoglobus fulgidus* (SEQ ID NO:37), at least 65% homology with the amino acid sequence of the ribonuclease H from *Thermococcus litoralis* (SEQ ID NO:47), at least 71% homology with the amino acid sequence of the ribonuclease H from *Thermococcus celer* (SEQ ID NO:57), or at least 71% homology with the amino acid sequence of the ribonuclease H from *Pyrococcus horikoshii* (SEQ ID NO:32) is encompassed by the present invention if it has a thermostable RNase H activity.

The polypeptide of the present invention can be produced, for example, by (1) purification from a culture of a microorganism producing the polypeptide of the present invention, or (2) purification from a culture of a transformant containing a nucleic acid encoding the polypeptide of the present invention.

(1) Purification from culture of microorganism producing the polypeptide of the present invention The microorganism producing the polypeptide of the present invention is exemplified by *Bacillus caldotenax* (DSM406), *Pyrococcus furiosus* (DSM3638), *Thermotoga maritima* (DSM3109), *Archaeoglobus fulgidus* (DSM4139), *Thermococcus litoralis* (DSM5473) or *Thermococcus celer* (DSM2476) which can be purchased from Deutsche Sammlung von Mikroorganismen und Zellkulturen GmbH, or *Pyrococcus horikoshii* (JCM9974) which can be purchased from the Institute of Physical and Chemical Research (RIKEN). The microorganism is cultured under conditions suitable for the growth of the microorganism. Preferably, culture conditions that increase the expression level of the polypeptide of interest are used. The polypeptide of interest produced in the cells or the culture medium can be purified according to a method conventionally used for purifying a protein.

A method conventionally used for culturing a thermostable bacterium can be utilized for the cultivation of the above-mentioned strain. Nutrients that can be utilized by the strain are added to the culture medium. For example, starch can be used as a carbon source, and Tryptone, peptone and yeast extract can be used as nitrogen sources. A metal salt such as a magnesium salt, a sodium salt or an iron salt may be added to a culture medium as a trace element. In addition, it may be advantageous to use artificial seawater for the preparation of a culture medium in case of a thermostable marine bacterium, for example.

The culture may be a standing culture or a spinner culture. For example, a dialysis culture method as described in Applied and Environmental Microbiology, 55:2086-2088 (1992) may be used. It is preferable to determine the culture conditions and the cultivation time depending on the strain or the composition of the culture medium to be used such that the productivity of the polypeptide becomes maximal.

A cell-free extract is first prepared in order to obtain a polypeptide. The cell-free extract can be prepared, for example, by collecting cells from a culture by centrifugation, filtration or the like and then disrupting the cells. A cell disruption method highly effective for extracting the enzyme of interest may be selected from sonication, disruption using beads, treatment with a lytic enzyme and the like. If the polypeptide is secreted into a culture supernatant, the polypeptide in the culture supernatant is concentrated by ammonium sulfate precipitation, ultrafiltration or the like. The concentrated polypeptide is used as a cell-free extract. A method conventionally used for purifying a protein can be used to isolate the polypeptide from the thus obtained cell-free extract. For example, ammonium sulfate precipitation, ion exchange chromatography, hydrophobic chromatography, gel filtration chromatography and the like can be used in combination.

(2) Purification from culture of transformant transformed with recombinant DNA containing nucleic acid encoding the polypeptide of the present invention The polypeptide of the present invention can be obtained from a transformant transformed with a recombinant DNA that contains a nucleic acid encoding the polypeptide of the present invention, for example, a nucleic acid having a nucleotide sequence of SEQ ID NO:8, 16, 22, 31, 36, 46, 56 or 58. A polypeptide having an amino acid sequence of SEQ ID NO:9 is produced using a nucleic acid having a nucleotide sequence of SEQ ID NO:8. A polypeptide having an amino acid sequence of SEQ ID NO:17 is produced using a nucleic acid having a nucleotide sequence of SEQ ID NO:16. A polypeptide having an amino acid sequence of SEQ ID NO:23 is produced using a nucleic acid having a nucleotide sequence of SEQ ID NO:22. A polypeptide having an amino acid sequence of SEQ ID NO:32 is produced using a nucleic acid having a nucleotide sequence of SEQ ID NO:31. A polypeptide having an amino acid sequence of SEQ ID NO:37 is produced using a nucleic acid having a nucleotide sequence of SEQ ID NO:36. A polypeptide having an amino acid sequence of SEQ ID NO:47 is produced using a nucleic acid having a nucleotide sequence of SEQ ID NO:46. A polypeptide having an amino acid sequence of SEQ ID NO:57 is produced using a nucleic acid having a nucleotide sequence of SEQ ID NO:56. A polypeptide having an amino acid sequence of SEQ ID NO:59 is produced using a nucleic acid having a nucleotide sequence of SEQ ID NO:58.

The polypeptide of the present invention may be purified from a culture obtained by culturing a transformant into which any one of the plasmids of the present invention pRHB11, pBCA3Nd2, pPFU220, pTM-RNH, pPHO238, pAFU204, pTLI204 and pTCE207 is transferred.

The host to be transformed is not limited to specific one and exemplified by those conventionally used in a field of recombinant DNA including *Escherichia coli*, *Bacillus subtilis*, yeast, filamentous fungi, plants, animals, cultured plant cells and cultured animal cells.

For example, the polypeptide of the present invention can be obtained using *Escherichia coli* harboring a plasmid in which the nucleic acid of the present invention is linked downstream from a lac promoter or a T7 phage promoter under conventional culture conditions, for example, in LB medium (10 g/l Tryptone, 5 g/l yeast extract, 5 g/l NaCl, pH 7.2) containing 100 µg/ml of ampicillin at 37° C. until logarithmic growth phase, adding isopropyl-β-D-thiogalactopyranoside at a final concentration of 1 mM thereto and further culturing at 37° C. to express the polypeptide in the cultured cells.

Cells are collected by centrifugation after cultivation, disrupted by sonication, and a supernatant collected by centrifugation is used as a cell-free extract. This cell-free extract exhibits a thermostable RNase H activity. The polypeptide of the present invention can be purified from the cell-free extract by using known methods such as ion exchange chromatography, gel filtration, hydrophobic chromatography and ammonium sulfate precipitation. Naturally, a partially purified product obtained during the purification process as described above also exhibits an RNase H activity. Since the polypeptide of the present invention expressed in *Escherichia coli* harboring a plasmid linked to the nucleic acid of the present invention is thermostable, the cultured cells and/or the cell-free extract may be heated, for example, at a temperature of 40° C. or above for about 10 minutes to remove heat-denatured insoluble proteins derived from the host in order to purify the polypeptide. An optimal temperature or time may be suitably selected for the heat treatment.

As described above, when the polypeptide of the present invention is expressed at normal temperature (e.g., 37° C.) using a transformant harboring a nucleic acid encoding the polypeptide, the resulting expression product retains the activity, the thermostability and the like. That is, the polypeptide of the present invention can assume its inherent higher-order structure even if it is expressed at a temperature quite different from the growth temperature of the original producer cell.

The nucleic acid of the present invention is a nucleic acid that encodes the polypeptide of the present invention. Specifically, it is (1) a nucleic acid that encodes a polypeptide having the amino acid sequence of SEQ ID NO:9, 17, 23, 32, 37, 47, 57 or 59, or an amino acid sequence in which at least one amino acid residue is deleted, added, inserted or substituted in the sequence and having a thermostable RNase H activity; (2) a nucleic acid having the nucleotide sequence of SEQ ID NO:8, 16, 22, 31, 36, 46, 56 or 58; (3) a nucleic acid that has a nucleotide sequence that is hybridizable to the nucleotide sequence of (1) or (2) above under stringent conditions, or that shares at least 69%, preferably 80%, more preferably 90% homology with the nucleotide sequence of (1) or (2) above, and that encodes a polypeptide having a thermostable RNase H activity, or the like.

The homology of the nucleotide sequence can be determined using a computer program DNASIS-Mac, or a computer algorithm FASTA (version 3.0) or BLAST (version 2.0).

As used herein, a nucleic acid means a single-stranded or double-stranded DNA or RNA. If the nucleic acid of (2) above is an RNA, it is represented by a nucleotide sequence in which T is replaced by U in the nucleotide sequence of SEQ ID NO:8, for example.

For example, the nucleic acid of the present invention can be obtained as follows.

The nucleic acid of (2) above having the nucleotide sequence of SEQ ID NO:8, 16, 22, 31, 36, 46, 56 or 58 can be isolated as follows. A genomic DNA is prepared according to a conventional method from *Bacillus caldotenax* (DSM406), *Pyrococcus furiosus* (DSM3638), *Thermotoga maritima* (DSM3109), *Archaeoglobus fulgidus* (DSM4139), *Thermococcus litoralis* (DSM5473), *Thermococcus celer* (DSM2476) or *Pyrococcus horikoshii* (JCM9974) cultured as described above for the polypeptide of the present invention. The genomic DNA is used to construct a DNA library. The nucleic acid can be isolated from the DNA library. Also, the nucleic acid can be obtained by amplifying a nucleic acid having a nucleotide sequence of SEQ ID NO:8, 16, 22, 31, 36, 46, 56 or 58 by a polymerase chain reaction (PCR) using the genomic DNA as a template.

Furthermore, a nucleic acid encoding a polypeptide having a thermostable RNase H activity similar to that of the polypeptide of the present invention can be obtained on the basis of the nucleotide sequence of the nucleic acid encoding the polypeptide of the present invention provided by the present invention (e.g., the nucleotide sequence of SEQ ID NO:8, 16, 22, 31, 36, 46, 56 or 58). Specifically, a DNA encoding a polypeptide having a thermostable RNase H activity can be screened by using the nucleic acid encoding the polypeptide of the present invention or a portion of the nucleotide sequence as a probe for hybridization from a DNA extracted from cells or PCR products obtained using the DNA as a template. Alternatively, a DNA encoding a polypeptide having a thermostable RNase H activity can be amplified using a gene amplification method such as a PCR using a primer designed based on the above-mentioned nucleotide sequence. Additionally, a DNA encoding a polypeptide having a thermostable RNase H activity can be chemically synthesized. The nucleic acids of (1) or (3) above can be obtained according to such a method.

A nucleic acid fragment containing only a portion of the nucleic acid of interest may be obtained according to the above-mentioned method. In this case, the entire nucleic acid of interest can be obtained as follows. The nucleotide sequence of the obtained nucleic acid fragment is determined to confirm that the fragment is a portion of the nucleic acid of interest. Hybridization is carried out using the nucleic acid fragment or a portion thereof as a probe. Alternatively, a PCR is carried out using a primer synthesized on the basis of the nucleotide sequence of the nucleic acid fragment.

"Hybridize under stringent conditions" refers to being capable of hybridizing under conditions as described in T. Maniatis et al. (eds.), Molecular Cloning: A Laboratory Manual 2nd ed., Cold Spring Harbor Laboratory (1989), for example, under the following conditions. A membrane onto which a nucleic acid is immobilized is incubated with a probe in 6×SSC (1×SSC: 0.15 M NaCl, 0.015 M sodium citrate, pH 7.0) containing 0.5% SDS, 0.1% bovine serum albumin (BSA), 0.1% polyvinylpyrrolidone, 0.1% Ficoll 400 and 0.01% denatured salmon sperm nucleic acid at 50° C. for 12 to 20 hours. After incubation, the membrane is washed in 2×SSC containing 0.5% SDS at 37° C. while changing the SSC concentration down to 0.1× and the temperature up to 50° C. until the signal from the immobilized nucleic acid can be distinguished from background, and the probe is then detected. The activity of the protein encoded by the thus obtained novel nucleic acid is determined as described above, thereby confirming whether or not the nucleic acid is the nucleic acid of interest.

If an oligonucleotide probe is used, "stringent conditions" refer to, for example, incubation at a temperature of [Tm−25° C.] overnight in a solution containing 6×SSC, 0.5% SDS, 5× Denhardt's and 0.01% denatured salmon sperm nucleic acid although it is not intended to limit the present invention.

Tm of an oligonucleotide probe or primer can be determined, for example, according to the following equation:

$$Tm=81.5-16.6(\log_{10}[Na^+])+0.41(\% \text{ G+C})-(600/N)$$

wherein N is the chain length of the oligonucleotide probe or primer; % G+C is the content of guanine and cytosine residues in the oligonucleotide probe or primer.

If the chain length of the oligonucleotide probe or primer is shorter than 18 bases, Tm can be estimated, for example, as the sum of the product of the number of A+T (adenine and thymine) residues multiplied by 2(° C.) and the product of the number of G+C residues multiplied by 4(° C.): [(A+T)×2+ (G+C)×4].

According to the present invention, a nucleic acid which is capable of hybridizing to the nucleic acid encoding the polypeptide of the present invention under stringent conditions is encompassed by the present invention as long as it encodes a polypeptide having a thermostable RNase H activity even if it does not have the same nucleotide sequence as that disclosed herein, as described above.

It is known that one to six codon(s) (a combination of three bases), which defines an amino acid in a gene, is assigned for each amino acid. Thus, many nucleic acids can encode one specific amino acid sequence although it depends on the amino acid sequence. Nucleic acids are not necessarily stable in the nature. Generation of a mutation in a nucleotide sequence is not unusual. A mutation generated in a nucleic acid may not alter the encoded amino acid sequence (called a silent mutation). In this case, it can be said that a different nucleic acid encoding the same amino acid sequence is generated. Thus, it cannot be denied that various nucleic acids encoding the same amino acid sequence can be generated in the course of passage of an organism containing a nucleic acid encoding one specific amino acid sequence. Furthermore, it is not difficult to artificially produce various nucleic acids encoding the same amino acid sequence if one uses various genetic engineering techniques.

For example, if a codon used in an original nucleic acid encoding a protein of interest is one whose codon usage is low in the host to be used for producing the protein by genetic engineering, the expression level of the protein may be low. In this case, the codon is artificially converted into one frequently used in the host without altering the encoded amino acid sequence aiming at elevating the expression level of the protein of interest (e.g., JP-B 7-102146). As described above, various nucleic acids encoding one specific amino acid sequence can be artificially prepared, of course. They may also be generated in the nature.

The nucleic acid encoding the polypeptide of the present invention (e.g., a nucleic acid having the nucleotide sequence of SEQ ID NO:7) can be ligated to an appropriate vector to construct a recombinant DNA. The vector to be used for the construction of the recombinant DNA is not specifically limited. For example, plasmid vectors, phage vectors and virus vectors can be used. A suitable vector for the object of the recombinant DNA is selected.

Furthermore, a transformant can be produced by introducing the recombinant DNA into an appropriate host. The host to be used for the production of a transformant is not specifically limited. Microorganisms such as bacteria, yeasts and filamentous fungi as well as cultured cells from animals, plants, insects and the like can be used. The polypeptide of the present invention can be produced in large quantities by culturing the transformant to produce the polypeptide of the present invention in the culture.

EXAMPLES

The following Examples illustrate the present invention in more detail, but are not to be construed to limit the scope thereof.

Example 1

Preparation of RNase H from Thermophile *Bacillus caldotenax*

*Bacillus caldotenax* YT-G (purchased from Deutsche Sammlung von Mikroorganismen; DSM406) was inoculated into 100 ml of a medium containing 0.2% Tryptone (Difco Laboratories) and 1.5% yeast extract (Difco Laboratories) (pH 6.5), cultured at 60° C. for 140 minutes with shaking and used as a pre-culture. 30 ml of the pre-culture was inoculated into 3 L of a medium having the same composition and cultured with aeration at 2.5 L/minute and stirring at 250 rpm at a temperature of 60° C. for 5 hours.

The cells were collected by centrifuging the culture at 5000×g for 15 minutes. 402 g (wet weight) of the cells were suspended in 1000 ml of 50 mM tris-HCl buffer (pH 7.5) containing 10 mM mercaptoethanol, 0.5 M NaCl, 1 mM EDTA and 20 µM PAPMSF and disrupted using MINI-Lab (APV GAULIN/RANNIE). Cell debris were removed by centrifugation to recover a supernatant.

A polyethylene imine solution was added to the resulting supernatant at a final concentration of 0.1%. After stirring, the mixture was allowed to stand for 1 hour. A supernatant was then recovered by centrifugation. Ammonium sulfate was added to the supernatant to 50% saturation. A precipitate obtained by centrifugation was dissolved in 20 mM tris-HCl buffer (pH 7.5) containing 10 mM mercaptoethanol, 0.1 mM EDTA, 50 mM NaCl and 10% glycerol. The solution was dialyzed against the same buffer. The dialyzed sample was loaded onto a 280-ml DE52 column (Whatman) equilibrated with the same buffer and non-adsorptive fractions were collected.

The column was further washed with 420 ml of the buffer used for the equilibration and washing fractions were collected. The non-adsorptive fractions and the washing fractions from the DE52 column chromatography were mixed together and loaded onto a 240-ml P-11 column (Whatman) equilibrated with 20 mM tris-HCl buffer (pH 7.5) containing 10 mM mercaptoethanol, 0.1 mM EDTA, 50 mM NaCl and 10% glycerol. Elution was then carried out using the equilibration buffer containing 0 to 0.5 M NaCl.

The resulting active fractions were placed in a dialysis tube. The tube was placed on solid polyethylene glycol 20000 for dehydration-concentration at 4° C. The enzyme concentrate was then loaded onto a 300-ml Superdex G-200 column (Amersham Pharmacia Biotech) equilibrated with 25 mM tris-HCl buffer (pH 7.5) containing 5 mM mercaptoethanol, 0.5 mM EDTA, 30 mM NaCl and 10% glycerol. Elution was carried out using the buffer used for equilibration to obtain active fractions. The active fractions were loaded onto a 15-ml Heparin-Sepharose column (Amersham Pharmacia Biotech) equilibrated with 20 mM tris-HCl buffer (pH 7.5) containing 10 mM mercaptoethanol, 0.1 mM EDTA, 50 mM NaCl and 10% glycerol. Elution was carried out using the equilibration buffer containing 0 to 0.5 M NaCl.

The resulting active fractions were loaded onto a 5-ml Hitrap-SP column (Amersham Pharmacia Biotech) equilibrated with 20 mM tris-HCl buffer (pH 7.5) containing 10 mM mercaptoethanol, 0.1 mM EDTA, 50 mM NaCl and 10% glycerol. Elution was carried out using the equilibration buffer containing 0 to 0.5 M NaCl. The resulting active fractions were loaded onto a 300-ml Superdex G-200 column (Amersham Pharmacia Biotech) equilibrated with 25 mM tris-HCl buffer (pH 7.5) containing 5 mM mercaptoethanol, 0.5 mM EDTA, 30 mM NaCl and 10% glycerol again. The resulting active fractions were used as an RNase H preparation (an enzyme solution).

A thermostable RNase H activity was measured as follows.

1 mg of poly(rA) or poly(dT) (both from Amersham Pharmacia Biotech) was dissolved in 1 ml of 40 mM tris-HCl (pH 7.7) containing 1 mM EDTA to prepare a poly(rA) solution and a poly(dT) solution.

The poly(rA) solution (to a final concentration of 20 μg/ml) and the poly(dT) solution (to a final concentration of 30 μg/ml) were then added to 40 mM tris-HCl (pH 7.7) containing 4 mM $MgCl_2$, 1 mM DTT, 0.003% BSA and 4% glycerol. The mixture was reacted at 37° C. for 10 minutes and then cooled to 4° C. at prepare a poly(rA)-poly(dT) solution.

1 μl of an enzyme solution was added to 100 μl of the poly(rA)-poly(dT) solution. The mixture was reacted at 40° C. for 10 minutes. 10 μl of 0.5 M EDTA was added thereto to terminate the reaction. Absorbance at 260 nm was then measured. As a control, 10 μl of 0.5 M EDTA was added to the reaction mixture, the resulting mixture was reacted at 40° C. for 10 minutes, and the absorbance was then measured. A value (difference in absorbance) was obtained by subtracting the absorbance for the control from the absorbance for the reaction in the absence of EDTA. Thus, the concentration of nucleotide released from poly(rA)-poly(dT) hybrid by the enzymatic reaction was determined on the basis of the difference in absorbance. One unit of an RNase H was defined as an amount of enzyme that increases $A_{260}$ corresponding to release of 1 nmol of ribonucleotide in 10 minutes calculated according to the following equation. If a diluted enzyme solution is used, the value obtained using the following equation was corrected based on the dilution rate:

Unit=[Difference in Absorbance×Reaction Volume (ml)]/0.0152

Example 2

Cloning of *Bacillus caldotenax* RNase HII Gene (1) Preparation of Genomic DNA from *Bacillus caldotenax*

*Bacillus caldotenax* YT-G (DSM406) was inoculated into 60 ml of LB medium (1% Tryptone, 0.5% yeast extract and 0.5% NaCl, pH 7.2) and cultured at 65° C. for 20 hours. After culturing, the culture was centrifuged to collect cells. The cells were suspended in 2 ml of 25% sucrose and 50 mM tris-HCl (pH 8.0). 0.2 ml of 10 mg/ml lysozyme chloride (Nacalai Tesque) in water was added thereto. The mixture was reacted at 20° C. for 1 hour. After reaction, 12 ml of a mixture containing 150 mM NaCl, 1 mM EDTA and 20 mM tris-HCl (pH 8.0), 0.1 ml of 20 mg/ml proteinase K (Takara Shuzo) and 1 ml of a 10% aqueous solution of sodium lauryl sulfate were added to the reaction mixture. The mixture was incubated at 37° C. for 1 hour. 2.1 ml of 5 M NaCl and 2 ml of a CTAB-NaCl solution [10% cetyltrimethylammonium bromide (Nacalai Tesque) and 0.7 M NaCl] were then added to the mixture and the resulting mixture was mixed thoroughly and incubated at 65° C. for 10 minutes. An equal volume of a mixture of chloroform/isoamyl alcohol (24:1, v/v) was added thereto. The resulting mixture was gently mixed for 10 minutes and then centrifuged for 10 minutes at 10,000×g. After centrifugation, an equal volume of a mixture of phenol saturated with 100 mM tris-HCl (pH 8.0)/chloroform/isoamyl alcohol (25:24:1, v/v) was added to the resulting supernatant. The resulting mixture was gently mixed for 10 minutes and then centrifuged for 10 minutes at 10,000×g. After centrifugation, a 0.6 volume of 2-propanol was added to the resulting supernatant. The resulting fibrous precipitate was wound using a glass bar, washed with 70% ethanol in water, air-dried and then dissolved in 0.5 ml of TE buffer to obtain a genomic DNA solution.

(2) Cloning of Middle Portion of RNase HII Gene

Oligonucleotides BsuII-3 and BsuII-6 represented by SEQ ID NOS:1 and 2 were synthesized on the basis of Motif I and Motif III, portions conserved among amino acid sequences of RNase HIIs from various organisms (Biochemistry, 38:605-608 (1999)).

A PCR was carried out in a volume of 100 μl using 1 μl of the *Bacillus caldotenax* genomic DNA solution as prepared in Example 2-(1) as a template, and 100 pmol each of BsuII-3 and BsuII-6 as primers. TaKaRa Taq (Takara Shuzo) was used as a DNA polymerase for the PCR according to the attached protocol. The PCR was carried out as follows: 50 cycles of 94° C. for 30 seconds, 45° C. for 30 seconds and 72° C. for 1 minute. After reaction, the reaction mixture was subjected to phenol treatment followed by ethanol precipitation to purify a DNA. The resulting DNA was blunt-ended using T4 DNA polymerase (Takara Shuzo) and then subjected to agarose gel electrophoresis to recover an amplified DNA fragment of about 0.4 kb from the gel. The about 0.4-kb DNA fragment was ligated with pUC119 (Takara Shuzo) digested with SmaI (Takara Shuzo) using T4 DNA ligase (Takara Shuzo). The ligation mixture was used to transform *Escherichia coli* JM109.

The resulting transformants were cultured to obtain a plasmid 21-12 into which the about 0.4-kb DNA fragment was inserted.

(3) Cloning of Upstream Portion of RNase HII Gene

The nucleotide sequence of the inserted fragment of about 0.4 kb in the plasmid 21-12 obtained in Example 2-(2) was determined. Oligonucleotides RNII-S1 and RNII-S2 represented by SEQ ID NOS:3 and 4 were synthesized on the basis of the determined nucleotide sequence.

The *Bacillus caldotenax* genomic DNA as prepared in Example 2-(1) was digested with BamHI (Takara Shuzo) and ligated with a Sau3AI cassette (Takara Shuzo) using T4 DNA ligase. A procedure was carried out according to the protocol attached to TaKaRa LA PCR in vitro cloning kit (Takara Shuzo) using the ligation mixture as a template, RNII-S2 as a primer for a primary PCR and RNII-S1 as a primer for a secondary PCR. A DNA was purified from the solution after the secondary PCR by phenol extraction followed by ethanol precipitation. The DNA was blunt-ended using T4 DNA polymerase and then subjected to agarose gel electrophoresis to recover an amplified DNA fragment of about 1.5 kb from the gel. The about 1.5-kb DNA fragment was ligated with pUC119 digested with SmaI using T4 DNA ligase. The ligation mixture was used to transform *Escherichia coli* JM109.

The resulting transformants were cultured to obtain a plasmid B25N16 into which the about 1.5-kb DNA fragment was inserted.

(4) Cloning of Entire RNase HII Gene

Oligonucleotides RNII-S5 and RNII-S6 represented by SEQ ID NOS:5 and 6 were synthesized on the basis of the nucleotide sequence of the inserted fragment of about 0.4 kb in the plasmid 21-12 as determined in Example 2-(3).

A PCR was carried out using the plasmid 21-12 as prepared in Example 2-(2) as a template, and RNII-S5 and RNII-S6 as primers. TaKaRa Ex Taq (Takara Shuzo) was used as a DNA polymerase for the PCR according to the attached protocol. The PCR was carried out as follows: 25 cycles of 94° C. for 30 seconds, 55° C. for 30 seconds and 72° C. for 30 seconds. After reaction, the reaction mixture was subjected to agarose gel electrophoresis. An amplified DNA fragment of about 0.3 kb was recovered from the gel. The about 0.3-kb DNA fragment was labeled with digoxigenin using DIG High-prime (Roche Diagnostics).

Southern hybridization was carried out for digests of the *Bacillus caldotenax* genomic DNA as prepared in Example 2-(1) with HindIII (Takara Shuzo), Sac I (Takara Shuzo), or HindIII and SacI using the digoxigenin-labeled DNA as a probe.

Hybridization and detection were carried out using DIG Luminescent Detection Kit (Roche Diagnostics) according to the protocol attached thereto.

As a result, DNA fragments of about 4.5 kb, about 5.8 kb and about 1.3 kb were hybridized with the probe for the digests with HindIII, SacI, and HindIII and SacI, respectively.

Based on these results, the *Bacillus caldotenax* genomic DNA was digested with HindIII and subjected to agarose gel electrophoresis to recover DNA fragments of about 4.5 kb from the gel. The resulting DNA fragments were digested with SacI and subjected to agarose gel electrophoresis to recover DNA fragments of about 1.3 kb from the gel. The resulting DNA fragments were ligated with pUC19 (Takara Shuzo) digested with HindIII and SacI using T4 DNA ligase. The ligation mixture was used to transform *Escherichia coli* HB101.

The resulting transformants were replica-plated onto Hybond-N (Amersham Pharmacia Biotech). Colony hybridization was then carried out using the above-mentioned digoxigenin-labeled probe according to a conventional method. A plasmid pRHB1 was prepared from the thus obtained positive clone.

The nucleotide sequence of the DNA inserted into pRHB1 was then determined. Comparison of the amino acid sequence deduced from the nucleotide sequence with the amino acid sequence of the RNase HII from *Bacillus subtilis* suggested that a region of about 40 bp from the initiation codon was missing in the DNA in pRHB1. Then, the full-length RNase HII gene was constructed as follows.

B25N16 as prepared in Example 2-(3) was digested with HindIII and subjected to agarose gel electrophoresis to recover a DNA fragment of about 160 bp from the gel. The about 160-bp DNA fragment was ligated with pRHB1 digested with HindIII using T4 DNA ligase. The ligation mixture was used to transform *Escherichia coli* HB101. Plasmids were prepared from the resulting transformants.

Next, an oligonucleotide RNII-Nde represented by SEQ ID NO:7 was synthesized on the basis of the presumed nucleotide sequence around the initiation codon. PCRs were carried out using the plasmids prepared from the transformants as templates, and RNII-Nde and RNII-S6 as primers. A plasmid from which a DNA fragment of about 0.7 kb was amplified was selected and designated as pRHB11.

The nucleotide sequence of the DNA fragment inserted into the thus obtained plasmid pRHB11 was determined. Analysis of the results revealed an open reading frame (ORF) presumably encoding RNase HII. The nucleotide sequence of this open reading frame is shown in SEQ ID NO:8. The amino acid sequence of RNase HII deduced from the nucleotide sequence is shown in SEQ ID NO:9.

*Escherichia coli* HB101 transformed with the plasmid pRHB11 is designated and indicated as *Escherichia coli* HB101/pRHB11, and deposited on Sep. 5, 2000 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7655.

(5) Expression of *Bacillus Caldotenax* RNase HII Gene

*Escherichia coli* HB101 transformed with pRHB11 or pRHB1 was inoculated into 5 ml of LB medium containing 100 µg/ml of ampicillin and cultured with shaking at 37° C. overnight. After cultivation, cells collected by centrifugation were suspended in 0.5 ml of TE buffer and sonicated. A supernatant obtained by centrifugation was used as a crude cell extract.

10 mM tris-HCl (pH 8.0), 1 mM DTT (Nacalai Tesque), 0.003% BSA (fraction V, Sigma), 4% glycerol, 20 µg/ml poly(dT) (Amersham Pharmacia Biotech) and 30 µg/ml poly (rA) (Amersham Pharmacia Biotech) were mixed together. The mixture was incubated at 37° C. for 10 minutes and used as a substrate solution for measuring an RNase H activity.

1 µl of 1 M $MnCl_2$ was added to 100 µl of the substrate solution. The mixture was incubated at 40° C. 10 µl of a 10-fold dilution of the crude cell extract was added to the mixture to initiate a reaction. After reacting at 40° C. for 30 minutes, 10 µl of 0.5 M EDTA was added thereto to terminate the reaction. Absorbance at 260 nm was then measured.

As a result, the absorbance at 260 nm from a reaction in which a crude cell extract prepared from *Escherichia coli* HB101 harboring pRHB11 was used was clearly higher than that from a reaction in which a crude cell extract prepared from *Escherichia coli* HB101 harboring pRHB1 was used. Thus, it was demonstrated that pRHB11 contained an RNase HII gene and that *Escherichia coli* harboring pRHB11 expressed an RNase H activity.

(6) Preparation of Purified RNase HII Preparation

*Escherichia coli* HB101 transformed with pRHB11 obtained in Example 2-(4) was inoculated into 1 L of LB medium containing 100 µg/ml of ampicillin and cultured with shaking at 37° C. for 16 hours. After cultivation, cells collected by centrifugation were suspended in 52.3 ml of a sonication buffer [50 mM tris-HCl (pH 8.0), 2 mM 2-mercaptoethanol, 10% glycerol, 2 mM phenylmethanesulfonyl fluoride] and sonicated. A supernatant obtained by centrifuging the sonicated suspension at 12,000 rpm for 10 minutes was heated at 60° C. for 15 minutes. It was then centrifuged again at 12,000 rpm for 10 minutes to collect a supernatant. Thus, 50.0 ml of a heated supernatant was obtained.

The solution was subjected to RESOURSE Q column (Amersham Pharmacia Biotech) equilibrated with Buffer C [50 mM tris-HCl (pH 8.0), 2 mM 2-mercaptoethanol, 10% glycerol] and chromatographed using FPLC system (Amersham Pharmacia Biotech). As a result, RNase HII flowed through the RESOURSE Q column.

51 ml of the flow-through RNase HII fraction was subjected to RESOURSE S column (Amersham Pharmacia Biotech) equilibrated with Buffer C and eluted with a linear gradient of 0 to 500 mM NaCl using FPLC system. A fraction containing RNase HII eluted with about 240 mM NaCl was obtained.

3.0 ml of the RNase HII fraction was subjected in two portions to PD-10 column (Amersham Pharmacia Biotech) equilibrated with Buffer C containing 50 mM NaCl. 7.0 ml the resulting eluate was subjected to HiTrap-heparin column (Amersham Pharmacia Biotech) equilibrated with Buffer C containing 50 mM NaCl and eluted with a linear gradient of 50 to 550 mM NaCl using FPLC system. A fraction containing RNase HII eluted with about 310 mM NaCl was obtained.

4.4 ml of the RNase HII fraction was concentrated by ultrafiltration using Centricon-10 (Amicon). 280 μl of the concentrate was subjected to Superdex 200 gel filtration column (Amersham Pharmacia Biotech) equilibrated with 50 mM tris-HCl (pH 8.0) containing 100 mM NaCl and 0.1 mM EDTA and eluted with the same buffer. As a result, RNase HII was eluted at a position corresponding to a molecular weight of 35 kilodalton. This molecular weight corresponds to that of the RNase HII in the monomeric form.

The thus eluted RNase HII was used as Bca RNase HII preparation.

The enzymatic activity of the thus obtained Bca RNase HII preparation was measured as follows.

100 μl of a reaction mixture [20 mM HEPES-potassium hydroxide (pH 7.8), 0.01% bovine serum albumin (Takara Shuzo), 1% dimethyl sulfoxide, 10 mM manganese chloride, 20 μg/ml poly(dT) (Amersham Pharmacia Biotech), 30 μg/ml poly(rA) (Amersham Pharmacia Biotech)] which had been incubated at 40° C. was added to 1 μl of the Bca RNase HII preparation. The mixture was reacted at 40° C. for 10 minutes. The reaction was then terminated by adding 10 μl of 0.5 M EDTA (pH 8.0). Absorbance at 260 nm was then measured.

As a result, an RNase H activity was observed for the Bca RNase HII preparation.

Example 3

Cloning of *Bacillus caldotenax* RNase HIII Gene (1) Cloning of Fragment of RNase HIII Gene Primers BsuIII-1, BsuIII-3, BsuIII-6 and BsuIII-8 represented by SEQ ID NOS:10 to 13 for screening a gene encoding RNase HIII were synthesized based on the amino acid sequences of regions well conserved among *Bacillus subtilis* and other organisms determined on the basis of the homology among the amino acid sequences of RNase HIIIs from *Bacillus subtilis* [Otani, N. et al., Biochemistry, 38:605-608 (1999)] and other organisms.

A first PCR was carried out in a volume of 50 μl using 200 ng of the *Bacillus caldotenax* genomic DNA as prepared in Example 2-(1) as a template, and 100 pmol each of BsuIII-1 and BsuIII-8 as primers. A second PCR was then carried out in a volume of 100 μl using 1 μl of the reaction mixture as a template, and 100 pmol each of BsuIII-3 and BsuIII-6 as primers. TaKaRa Taq polymerase (Takara Shuzo) was used as a DNA polymerase for the two PCRs according to the attached protocol. The PCRs were carried out as follows: 25 (the first PCR) or 30 (the second PCR) cycles of 94° C. for 30 seconds, 45° C. for 30 seconds and 72° C. for 1 minute.

An amplified DNA fragment of about 450 bp was blunt-ended using T4 DNA polymerase (Takara Shuzo) and then subjected to agarose gel electrophoresis to recover the amplified DNA fragment of about 450 bp. The about 450-bp DNA fragment was ligated with pUC119 (Takara Shuzo) digested with SmaI (Takara Shuzo) using T4 DNA ligase (Takara Shuzo). The ligation mixture was used to transform *Escherichia coli* JM109.

The resulting transformants were cultured to obtain a plasmid pBCA3204 into which the about 450-bp DNA fragment was inserted.

(2) Cloning of RNase HIII Gene using Southern Hybridization Method

The nucleotide sequence of the DNA fragment inserted in pBCA3204 obtained in Example 3-(1) was determined. Primers RNIII-S3 and BcaRNIII-3 represented by SEQ ID NOS: 14 and 15 were synthesized on the basis of the determined nucleotide sequence. A PCR was carried out in a volume of 100 μl using RNIII-S3 and BcaRNIII-3 as primers and pBCA3204 as a template. TaKaRa Z-Taq (Takara Shuzo) was used as a DNA polymerase for the PCR according to the attached protocol. The PCR was carried out as follows: 30 cycles of 98° C. for 0 second, 55° C. for 0 second and 72° C. for 20 seconds. After reaction, the reaction mixture was subjected to phenol-chloroform extraction, ethanol precipitation and agarose gel electrophoresis to recover a DNA fragment of about 0.4 kb from the gel. The about 0.4-kb DNA fragment was labeled using DIG DNA Labeling Kit (Boehringer Mannheim) to prepare a probe.

20 μg of the *Bacillus caldotenax* genomic DNA prepared in Example 2-(1) was completely digested with BamHI, EcoRI, HindIII, PstI or XbaI (all from Takara Shuzo). The half of each of the digests was then subjected to agarose gel electrophoresis. The DNAs were transferred from the agarose gel to a nylon membrane using 0.4 N NaOH and fixed at 120° C. for 30 minutes. The membrane was pre-incubated in a sealed bag containing 30 ml of a hybridization buffer [43.4 g/L sodium chloride, 17.6 g/L sodium citrate, 1% blocking agent (Boehringer Mannheim), 0.1% N-lauroyl sarcosine, 0.02% sodium lauryl sulfate (SDS)] at 60° C. for 4 hours and then incubated in a sealed bag containing 5 ml of a hybridization buffer containing the probe at 60° C. for 16 hours.

The membrane was washed twice in 50 ml of 2×SSC (17.5 g/L NaCl, 7.7 g/L sodium citrate) containing 0.1% SDS at room temperature, and twice in 50 ml of 0.5×SSC (4.4 g/L sodium chloride, 1.9 g/L sodium citrate) containing 0.1% SDS at 45° C. Then, an EcoRI fragment of about 8 kb, a PstI fragment of about 4.5 kb and a HindIII fragment of about 1 kb which have sequences complementary to the probe were detected using DIG nucleic acid detection kit (Boehringer Mannheim).

The remaining half of the *Bacillus caldotenax* genomic DNA completely digested with PstI was subjected to agarose gel electrophoresis. PstI fragments of about 4.5 kb were recovered from the gel. The DNA fragments were then ligated with a plasmid vector pTV119N, which had been digested with PstI and dephosphorylated with alkaline phosphatase (Takara Shuzo). The ligation mixture was used to transform *Escherichia coli* JM109.

A PCR was carried out in a volume of 50 μl using RNIII-S3 and BcaRNIII-3 as primers, and one of the colonies as a template to select a colony presumably harboring an RNase HIII gene. TaKaRa-Z Taq (Takara Shuzo) was used for the PCR according to the attached protocol. The PCR was carried out as follows: 30 cycles of 98° C. for 0 second, 55° C. for 0 second and 72° C. for 20 seconds. As a result, it was found that the gene of interest was contained in the colony No. 88.

A PCR was carried out using a plasmid prepared from the colony No. 88 as a template, and a primer pair RN-N (Takara Shuzo) and BcaRNIII-3 or a primer pair M4 (Takara Shuzo) and RNIII-S3 to examine whether or not the entire RNase HIII gene was contained in the plasmid. As a result, it anticipated based on the length of the amplification product that the entire RNase HIII gene was contained in the plasmid, which was designated as pBCA3P88.

(3) Determination of Nucleotide Sequence of DNA Fragment Containing RNase HIII Gene The nucleotide sequence of the DNA fragment inserted into the plasmid pBCA3P88 obtained in Example 3-(2) was determined according to a dideoxy method.

Analysis of the determined nucleotide sequence revealed the existence of an open reading frame encoding an amino acid sequence including the N-terminal amino acid sequence of RNase HIII. The nucleotide sequence of the open reading frame and the amino acid sequence of RNase HIII deduced from the nucleotide sequence are shown in SEQ ID NO:16 and SEQ ID NO:17, respectively.

(4) Construction of Plasmid for Expressing RNase HIII

A PCR was carried out in a volume of 100 µl using the plasmid pBCA3P88 as described in Example 3-(2) as a template, BcaRNIIINde represented by SEQ ID NO:18 designed with reference to the sequence around the above-mentioned open reading frame for RNase HIII and M13 primer M4 (Takara Shuzo). Pyrobest DNA polymerase (Takara Shuzo) was used as a DNA polymerase for the PCR according to the attached protocol. The PCR was carried out as follows: 30 cycles of 94° C. for 30 seconds, 55° C. for 30 seconds and 72° C. for 3 minutes. An amplified DNA fragment of about 4 kb was digested with NdeI (Takara Shuzo) and subjected to agarose gel electrophoresis to recover an NdeI fragment of about 1.4 kb from the gel. The about 1.4-kb DNA fragment was ligated with pTV119Nd (a plasmid in which the NcoI site in pTV119N is converted into a NdeI site) which had been digested with NdeI and dephosphorylated with alkaline phosphatase (Takara Shuzo). The ligation mixture was used to transform *Escherichia coli* JM109.

Next, a PCR was carried out in a volume of 50 µl using one of the colonies as a template, and RV-N (Takara Shuzo) and BcaRNIII-3 (SEQ ID NO:15) as primers in order to screen for a plasmid in which the RNase HIII gene in the NdeI fragment was linked downstream from the lac promoter in the vector pTV119Nd. A colony presumably harboring the RNase HIII gene was then selected. TaKaRa-Z Taq (Takara Shuzo) was used as a DNA polymerase for the PCR according to the attached protocol. The PCR was carried out as follows: 30 cycles of 98° C. for 0 second, 55° C. for 0 second and 72° C. for 20 seconds. As a result, it was found that the colony No. 2 contained a plasmid in which the RNase HIII gene in the NdeI fragment was linked downstream from the lac promoter in the vector pTV119Nd. This plasmid was designated as pBCA3Nd2.

The determination of the nucleotide sequence of the DNA fragment inserted into the plasmid by a dideoxy method revealed that there was no mutation due to the PCR except that the initiation codon GTG was changed to ATG.

*Escherichia coli* JM109 transformed with the plasmid pBCA3Nd2 is designated and indicated as *Escherichia coli* JM109/pBCA3Nd2, and deposited on Sep. 5, 2000 (date of original deposit) at International Patent Organism Depositary, National Institute of Advanced Industrial Science and Technology, AIST Tsukuba Central 6, 1-1, Higashi 1-chome, Tsukuba-shi, Ibaraki-ken 305-8566, Japan under accession number FERM BP-7653.

(5) Preparation of Purified RNase HIII Preparation

*Escherichia coli* JM109 transformed with pBCA3Nd2 obtained in Example 3-(4) was inoculated into 2 L of LB medium containing 100 µg/ml of ampicillin and cultured with shaking at 37° C. for 16 hours. After cultivation, cells collected by centrifugation were suspended in 39.6 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12,000 rpm for 10 minutes was heated at 60° C. for 15 minutes. It was then centrifuged again at 12,000 rpm for 10 minutes to collect a supernatant. Thus, 39.8 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HIII flowed through the RESOURSE Q column.

45 ml of the flow-through RNase HIII fraction was dialyzed against 2 L of Buffer B [50 mM tris-HCl (pH 7.0), 1 mM EDTA] for 2 hours. The dialysis was repeated for two more times under the same conditions. 55.8 ml of the dialyzed enzyme solution was subjected to RESOURSE S column (Amersham Pharmacia Biotech) equilibrated with Buffer B and eluted with a linear gradient of 0 to 500 mM NaCl using FPLC system. A fraction containing RNase HIII eluted with about 105 mM NaCl was obtained.

Buffer B containing 1 M NaCl was added to 7.0 ml of the fraction to make the NaCl concentration to 150 mM. The mixture was subjected to HiTrap-heparin column (Amersham Pharmacia Biotech) equilibrated with Buffer B containing 150 mM NaCl. As a result, RNase HIII flowed through the HiTrap-heparin column.

7.5 ml of the flow-through RNase HIII fraction was concentrated by ultrafiltration using Centricon-10 (Millipore). 190 µl of the concentrate was subjected to Superdex 200 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HIII was eluted at a position corresponding to a molecular weight of 33 kilodalton. This molecular weight corresponds to that of the RNase HIII in the monomeric form.

The thus eluted RNase HIII was used as Bca RNase HIII preparation.

The enzymatic activity of the thus obtained Bca RNase HIII preparation was measured as follows.

100 µl of a reaction mixture [20 mM HEPES-potassium hydroxide (pH 7.8), 0.01% bovine serum albumin (Takara Shuzo), 1% dimethyl sulfoxide, 4 mM magnesium acetate, 20 µg/ml poly(dT) (Amersham Pharmacia Biotech), 30 µg/ml poly(rA) (Amersham Pharmacia Biotech)] which had been incubated at 40° C. was added to 1 µl of the Bca RNase HIII preparation. The mixture was reacted at 40° C. for 10 minutes. The reaction was terminated by adding 10 µl of 0.5 M EDTA (pH 8.0). Absorbance at 260 nm was then measured.

As a result, an RNase H activity was observed for the Bca RNase HIII preparation.

Example 4

Cloning of *Pyrococcus Furiosus* RNase HII Gene (1) Preparation of Genomic DNA from *Pyrococcus Furiosus*

2 L of a medium containing 1% Tryptone (Difco Laboratories), 0.5% yeast extract (Difco Laboratories), 1% soluble starch (Nacalai Tesque), 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_4$, 0.1 ppm $Na_2MoO_4.2H_2O$ and 0.25 ppm $NiCl_2.6H_2O$ was placed in a 2-L medium bottle, sterilized at 120° C. for 20 minutes, bubbled with nitrogen gas to remove dissolved oxygen, then *Pyrococcus furiosus* (purchased from Deutsche Sammlung von Mikroorganismen; DSM3638) was inoculated into the medium and cultured at 95° C. for 16 hours without shaking. After cultivation, cells were collected by centrifugation.

The resulting cells were then suspended in 4 ml of 25% sucrose, 50 mM tris-HCl (pH 8.0). 0.4 ml of 10 mg/ml lysozyme chloride (Nacalai Tesque) in water was added thereto. The mixture was reacted at 20° C. for 1 hour. After reaction, 24 ml of a mixture containing 150 mM NaCl, 1 mM EDTA and 20 mM tris-HCl (pH 8.0), 0.2 ml of 20 mg/ml proteinase K (Takara Shuzo) and 2 ml of 10% aqueous solution of sodium lauryl sulfate were added to the reaction mixture. The mixture was incubated at 37° C. for 1 hour.

After reaction, the mixture was subjected to phenol-chloroform extraction followed by ethanol precipitation to prepare about 1 mg of genomic DNA.

(2) Cloning of RNase HII Gene

The entire genomic sequence of *Pyrococcus horikoshii* was published [Kawarabayashi, Y. et al., DNA Research, 5:55-76 (1998)]. The existence of one gene encoding a homologue of RNase HII (PH1650) in the genome was known (SEQ ID NO:19, the home page of National Institute of Technology and Evaluation: www.nite.go.jp/).

Homology between the PH1650 gene (SEQ ID NO:19) and the partially published genomic sequence of *Pyrococcus furiosus* (the home page of University of Utah, Utah Genome Center: www.genome.utah.edu/sequence.html) was searched. As a result, a highly homologous sequence was found.

Primers 1650Nde (SEQ ID NO:20) and 1650Bam (SEQ ID NO:21) were synthesized on the basis of the homologous sequence.

A PCR was carried out in a volume of 100 µl using 200 ng of the *Pyrococcus furiosus* DNA obtained in Example 4-(1) as a template, and 20 pmol each of 1650Nde and 1650Bam as primers. TaKaRa Ex Taq (Takara Shuzo) was used as a DNA polymerase for the PCR according to the attached protocol. The PCR was carried out as follows: 30 cycles of 94° C. for 30 seconds, 55° C. for 30 seconds and 72° C. for 1 minute. An amplified DNA fragment of about 0.7 kb was digested with NdeI and BamHI (both from Takara Shuzo). The resulting DNA fragment was inserted between the NdeI site and the BamHI site in a plasmid vector pET3a (Novagen) to make a plasmid pPFU220.

(3) Determination of Nucleotide Sequence of DNA Fragment Containing RNase HII Gene The nucleotide sequence of the DNA fragment inserted into pPFU220 obtained in Example 4-(2) was determined according to a dideoxy method.

Analysis of the determined nucleotide sequence revealed the existence of an open reading frame presumably encoding RNase HII. The nucleotide sequence of the open reading frame is shown in SEQ ID NO:22. The amino acid sequence of RNase HII deduced from the nucleotide sequence is shown in SEQ ID NO:23.

*Escherichia coli* JM109 transformed with the plasmid pPFU220 is designated and indicated as *Escherichia coli* JM109/pPFU220, and deposited on Sep. 5, 2000 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7654.

(4) Preparation of Purified RNase HII Preparation

*Escherichia coli* HMS174(DE3) (Novagen) was transformed with pPFU220 obtained in Example 4-(2). The resulting *Escherichia coli* HMS174(DE3) harboring pPFU220 was inoculated into 2 L of LB medium containing 100 ug/ml of ampicillin and cultured with shaking at 37° C. for 16 hours. After cultivation, cells collected by centrifugation were suspended in 66.0 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12,000 rpm for 10 minutes was heated at 80° C. for 15 minutes. It was then centrifuged again at 12,000 rpm for 10 minutes to collect a supernatant. Thus, 61.5 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

60.0 ml of the flow-through RNase HII fraction was subjected to RESOURSE S column (Amersham Pharmacia Biotech) equilibrated with Buffer A and eluted with a linear gradient of 0 to 500 mM NaCl using FPLC system. A fraction containing RNase HII eluted with about 150 mM NaCl was obtained.

2.0 ml of the RNase HII fraction was concentrated by ultrafiltration using Centricon-10 (Millipore). 250 µl of the concentrate was subjected to Superdex 200 gel filtration column (Amersham Pharmacia Biotech) equilibrated with 50 mM tris-HCl (pH 8.0) containing 100 mM NaCl and 0.1 mM EDTA and eluted with the same buffer. As a result, RNase HII was eluted at a position corresponding to a molecular weight of 17 kilodalton. This molecular weight corresponds to that of the RNase HII in the monomeric form.

The thus eluted RNase HII was used as Pfu RNase HII preparation.

The enzymatic activity of the thus obtained Pfu RNase HII preparation was measured as described in Example 3-(5). As a result, an RNase H activity was observed for the Pfu RNase HII preparation.

Example 5

Cloning of *Thermotoga Maritima* RNase HII Gene (1) Preparation of Genomic DNA from *Thermotoga maritima*

2 L of a medium containing 1% Tryptone, 0.5% yeast extract, 1% soluble starch, 3.5% Jamarine S Solid, 0.5% Jamarine S Liquid, 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_3$, 0.1 ppm $Na_2MoO_4.2H_2O$ and 0.25 ppm $NiCl_2.6H_2O$ was placed in a 2-L medium bottle, sterilized at 120° C. for 20 minutes, bubbled with nitrogen gas to remove dissolved oxygen, then *Thermotoga maritima* (purchased from Deutsche Sammlung von Mikroorganismen und Zellkulturen GmbH; DSM3109) was inoculated into the medium and cultured at 85° C. for 16 hours without shaking.

Cells collected by centrifugation from 300 ml of the culture were then suspended in 3 ml of TE buffer [10 mM tris-HCl (pH 7.5), 1 mM EDTA]. 150 µl of 10% aqueous solution of sodium lauryl sulfate (Nacalai Tesque) and 15 µl of 20 mg/ml proteinase K (Takara Shuzo) were added thereto. The mixture was incubated at 37° C. for 1 hour.

After reaction, 0.5 ml of 5 M NaCl was added to the mixture. After thoroughly mixing, 0.4 ml of a CTAB-NaCl solution [10% cetyltrimethylammonium bromide (Nacalai Tesque), 0.7 M NaCl] was added to the mixture. After thoroughly mixing, the mixture was incubated at 65° C. for 10 minutes. 1.5 ml of a mixture of chloroform/isoamyl alcohol (24:1, v/v) was added thereto. The mixture was gently mixed for 10 minutes and centrifuged at 20,000×g for 5 minutes. After centrifugation, an equal volume of a mixture of phenol saturated with 100 mM tris-HCl (pH 8.0)/chloroform/ isoamyl alcohol (25:24:1, v/v) was added to the resulting supernatant. The mixture was gently mixed for 10 minutes and then centrifuged at 20,000×g for 5 minutes. After centrifugation, a 0.6 volume of 2-propanol was added to the supernatant. The precipitate obtained by centrifugation at 10,000×g for 5 minutes was washed with 70% ethanol in water, air-dried and then dissolved in 200 µl of TE to obtain a genomic DNA solution.

(2) Cloning of RNase HII Gene

Oligonucleotides 915-F1, 915-F2, 915-R1 and 915-R2 represented by SEQ ID NOS:24 to 27 were synthesized on the basis of the nucleotide sequence of a portion that had been identified as an RNase HII gene in the nucleotide sequence of the genomic DNA of *Thermotoga maritima* (www.tigr.org/tdb/CMR/btm/htmls/SplashPage.html) in order to obtain an amplified DNA fragment containing an RNase HII gene by carrying out a PCR using the *Thermotoga maritima* genomic DNA as a template.

PCRs were carried out using the *Thermotoga maritima* genomic DNA as prepared in Example 5-(1) as a template, and 915-F1 and 915-R1, 915-F1 and 915-R2, 915-F2 and 915-R1, or 915-F2 and 915-R2 as a primer pair. TaKaRa Ex Taq (Takara Shuzo) was used as a DNA polymerase for the PCRs according to the attached protocol. The PCRs were carried out as follows: 25 cycles of 95° C. for 0.5 minute, 55° C. for 0.5 minute and 72° C. for 1.5 minute. After reactions, the respective PCR products were subjected to agarose gel electrophoresis to extract and purify amplified DNA fragments of about 0.7 kb.

The DNAs amplified using a primer pair 915-F1 and 915-R1 or 915-F1 and 915-R2 were digested with HindIII and XbaI (both from Takara Shuzo) and ligated with pUC19 (Takara Shuzo) digested with HindIII and XbaI using T4 DNA ligase (Takara Shuzo). The ligation mixture was used to transform *Escherichia coli* JM109.

The resulting transformants were cultured to prepare plasmid DNAs into which the about 0.7-kb DNA fragments were inserted. As a result, plasmids No. 1 and No. 2 having DNA fragments amplified using 915-F1 and 915-R1, and plasmids No. 3 and No. 4 having DNAs amplified using 915-F1 and 915-R2 were obtained.

In addition, the DNAs amplified using a primer pair 915-F2 and 915-R1 or 915-F2 and 915-R2 were doubly digested with NcoI (Takara Shuzo) and XbaI and ligated with pTV119N (Takara Shuzo) doubly digested with NcoI and XbaI using T4 DNA ligase. The ligation mixture was used to transform *Escherichia coli* JM109.

The resulting transformants were cultured to prepare plasmid DNAs into which the about 0.7-kb DNA fragments were inserted. As a result, plasmids No. 5 and No. 6 having DNA fragments amplified using 915-F2 and 915-R1, and a plasmid No. 7 having a DNA amplified using 915-F2 and 915-R2 were obtained.

*Escherichia coli* JM109 transformed with the plasmid No. 7 is designated and indicated as *Escherichia coli* JM109/pTM-RNH, and deposited on Sep. 5, 2000 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7652.

(3) Expression of *Thermotoga maritima* RNase HII Gene

*Escherichia coli* JM109 transformed with one of the plasmids No. 1 to 7 or pUC19 was inoculated into 5 ml of LB medium (10 g/L Tryptone, 5 g/L yeast extract, 5 g/L NaCl, pH 7.2) containing 100 µg/ml of ampicillin and cultured with shaking at 37° C. When the absorbance at 660 nm reached 0.5, isopropyl-β-D-thiogalactopyranoside was added thereto to a final concentration of 1 mM and the cells were cultured overnight. After cultivation, cells collected by centrifugation were suspended in 1 ml of TE buffer and sonicated. The sonicated suspension was heated at 80° C. for 10 minute. A supernatant obtained by centrifugation was used as a crude cell extract.

Absorbance was measured using the crude cell extract as described in Example 2-(5).

As a result, when reactions were carried out in the presence of $MnCl_2$, the absorbance at 260 nm from each of the reactions in which crude cell extracts prepared from *Escherichia coli* JM109 harboring the plasmid No. 3, 5, 6 or 7 were used was clearly higher than that from a reaction in which a crude extract prepared from *Escherichia coli* JM109 harboring pUC19 was used. Thus, it was demonstrated that the plasmids No. 3, 5, 6 and 7 contained RNase HII genes and that *Escherichia coli* harboring one of these plasmids expressed an RNase H activity.

The nucleotide sequences of the DNA fragments inserted into the plasmids which were demonstrated to express RNase H activities in *Escherichia coli* were determined. Analysis of the determined nucleotide sequences revealed an open reading frame presumably encoding RNase HII. The nucleotide sequence of the open reading frame is shown in SEQ ID NO:58. The amino acid sequence of RNase HII deduced from the nucleotide sequence is shown in SEQ ID NO:59. Then, it was found that one base substitution that was presumably generated upon the PCR was observed in the nucleotide sequence of the DNA fragment inserted in the plasmid No. 7, resulting in the change in the encoded amino acid residue.

(4) Preparation of Purified RNase HII Preparation

*Escherichia coli* JM109 was transformed with the plasmid No. 7 (pTM-RNH) obtained in Example 5-(2). The resulting *Escherichia coli* JM109 harboring pTM-RNH was inoculated into 1 L of LB medium containing 100 µg/ml of ampicillin and cultured with shaking at 37° C. for 16 hours. After cultivation, cells collected by centrifugation were suspended in 31.0 ml of a sonication buffer [50 mM tris-HCl (pH 8.0), 2 mM 2-mercaptoethanol, 10% glycerol, 2 mM phenylmethanesulfonyl fluoride] and sonicated. A supernatant obtained by centrifuging the sonicated suspension at 12,000 rpm for 10 minutes was heated at 70° C. for 15 minutes. It was then centrifuged again at 12,000 rpm for 10 minutes to collect a supernatant. Thus, 32.0 ml of a heated supernatant was obtained.

The heated supernatant was subjected to RESOURSE Q column (Amersham Pharmacia Biotech) equilibrated with Buffer C [50 mM tris-HCl (pH 8.0), 2 mM 2-mercaptoethanol, 10% glycerol] and chromatographed using FPLC system (Amersham Pharmacia Biotech). As a result, RNase HII flowed through the RESOURSE Q column.

32.5 ml of the flow-through RNase HII fraction was subjected to RESOURSE S column (Amersham Pharmacia Biotech) equilibrated with Buffer C and eluted with a linear gradient of 0 to 500 mM NaCl using FPLC system. A fraction containing RNase HII eluted with about 240 mM NaCl was obtained.

2.0 ml of the RNase HII fraction was subjected to PD-10 column (Amersham Pharmacia Biotech) equilibrated with Buffer C containing 50 mM NaCl. 3.5 ml of the resulting eluate was subjected to HiTrap-heparin column (Amersham Pharmacia Biotech) equilibrated with Buffer C containing 50 mM NaCl and eluted with a linear gradient of 50 to 550 mM NaCl using FPLC system. As a result, a fraction containing RNase HII eluted with about 295 mM NaCl was obtained.

The thus eluted RNase HII was used as Tma RNase HII preparation.

The enzymatic activity of the thus obtained Tma RNase HII preparation was measured as described in Example 2-(6). As a result, an RNase H activity was observed for the Tma RNase HII preparation.

Example 6

Cloning of RNase HII Gene from *Pyrococcus horikoshii*

(1) Preparation of Genomic DNA from *Pyrococcus horikoshii*

2 L of a medium containing 1% Tryptone (Difco Laboratories), 0.5% yeast extract (Difco Laboratories), 1% soluble starch (Nacalai Tesque), 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_4$, 0.1 ppm $Na_2MoO_4.2H_2O$ and 0.25 ppm $NiCl_2.6H_2O$ was placed in a 2-L medium bottle, sterilized at 120° C. for 20 minutes, bubbled with nitrogen gas to remove dissolved oxygen, then *Pyrococcus horikoshii* OT3 (purchased from the Institute of Physical and Chemical Research (RIKEN); JCM9974) was inoculated into the medium and cultured at 95° C. for 16 hours without shaking. After cultivation, cells were collected by centrifugation.

The cells were then suspended in 4 ml of 25% sucrose, 50 mM tris-HCl (pH 8.0). 0.4 ml of 10 mg/ml lysozyme chloride (Nacalai Tesque) in water was added thereto. The mixture was reacted at 20° C. for 1 hour. After reaction, 24 ml of a mixture containing 150 mM NaCl, 1 mM EDTA and 20 mM tris-HCl (pH 8.0), 0.2 ml of 20 mg/ml proteinase K (Takara Shuzo) and 2 ml of 10% aqueous solution of sodium lauryl sulfate were added to the reaction mixture. The mixture was incubated at 37° C. for 1 hour.

After reaction, the mixture was subjected to phenol-chloroform extraction followed by ethanol precipitation to prepare about 1 mg of genomic DNA.

(2) Cloning of RNase HII Gene

The entire genomic sequence of the *Pyrococcus horikoshii* has been published [DNA Research, 5:55-76 (1998)]. The existence of one gene encoding a homologue of RNase HII (PH1650) was known (SEQ ID NO:28, the home page of National Institute of Technology and Evaluation: www.nite.go.jp/).

Primers PhoNde (SEQ ID NO:29) and PhoBam (SEQ ID NO:30) were synthesized on the basis of the sequence of the PH1650 gene (SEQ ID NO:28).

A PCR was carried out using 100 ng of the *Pyrococcus horikoshii* DNA prepared in Example 6-(1) as a template, and 20 pmol each of PhoNde and PhoBam as primers in a volume of 100 µl. TaKaRa Ex Taq (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.7 kb was digested with NdeI and BamHI (both from Takara Shuzo). Then, a plasmid pPHO238 was constructed by incorporating the resulting DNA fragment between NdeI and BamHI sites in a plasmid vector pET3a (Novagen).

(3) Determination of Nucleotide Sequence of DNA Fragment Containing RNase HII Gene The nucleotide sequence of the DNA fragment inserted into pPHO238 obtained in Example 6-(2) was determined according to a dideoxy method.

Analysis of the determined nucleotide sequence revealed an open reading frame presumably encoding RNase HII. The nucleotide sequence of the open reading frame is shown in SEQ ID NO:31. The amino acid sequence of RNase HII deduced from the nucleotide sequence is shown in SEQ ID NO:32.

*Escherichia coli* JM109 transformed with the plasmid pPHO238 is designated and indicated as *Escherichia coli* JM109/pPHO238, and deposited on Feb. 22, 2001 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7692.

(4) Preparation of Purified RNase HII Preparation

*Escherichia coli* HMS174(DE3) (Novagen) was transformed with pPHO238 obtained in Example 6-(2). The resulting *Escherichia coli* HMS174(DE3) harboring pPHO238 was inoculated into 1 L of LB medium containing 100 µg/ml of ampicillin and cultured with shaking at 37° C. for 16 hours. After cultivation, cells collected by centrifugation were suspended in 34.3 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12,000 rpm for 10 minutes was heated at 80° C. for 15 minutes. It was then centrifuged again at 12,000 rpm for 10 minutes to collect a supernatant. Thus, 33.5 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

35.0 ml of the flow-through RNase HII fraction was dialyzed against 2 L of Buffer B (50 mM tris-HCl (pH 7.0), 1 mM EDTA) for 2 hours. The dialysis was repeated two more times. 34.5 ml of the dialyzed enzyme solution was subjected to RESOURSE S column (Amersham Pharmacia Biotech) equilibrated with Buffer B and eluted with a linear gradient of 0 to 500 mM NaCl using FPLC system. A fraction containing RNase HII eluted with about 155 mM NaCl was obtained.

Buffer B was added to 4.0 ml of the fraction to make the NaCl concentration to 50 mM. The mixture was subjected to HiTrap-heparin column (Amersham Pharmacia Biotech) equilibrated with Buffer B containing 50 mM NaCl and eluted with a linear gradient of 50 to 550 mM NaCl using FPLC system. As a result, a fraction containing RNase HII eluted with about 160 mM NaCl was obtained.

6.9 ml of the RNase HII fraction was concentrated by ultrafiltration using Centricon-10 (Millipore). Two portions each separated from 250 µl of the concentrate were subjected to Superose 6 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HII was eluted at a position corresponding to a molecular weight of 24.5 kilodalton. This molecular weight corresponds to that of the RNase HII in the monomeric form.

The RNase HII eluted as described above was used as Pho RNase HII preparation.

The enzymatic activity of the thus obtained Pho RNase HII preparation was measured as described in Example 3-(5). As a result, an RNase H activity was observed for the Pho RNase HII preparation.

Example 7

Cloning of RNase HII Gene from *Archaeoglobus fulgidus*

(1) Preparation of Genomic DNA from *Archaeoglobus fulgidus*

Cells of *Archaeoglobus Fulgidus* (purchased from Deutsche Sammlung von Mikroorganismen und Zellkulturen GmbH; DSM4139) collected from 8 ml of a culture was suspended in 100 µl of 25% sucrose, 50 mM tris-HCl (pH 8.0). 20 µl of 0.5 M EDTA and 10 µl of 10 mg/ml lysozyme chloride (Nacalai Tesque) in water was added thereto. The mixture was reacted at 20° C. for 1 hour. After reaction, 800 µl of a mixture containing 150 mM NaCl, 1 mM EDTA and 20 mM tris-HCl (pH 8.0), 10 µl of 20 mg/ml proteinase K (Takara Shuzo) and 50 µl of 10% aqueous solution of sodium lauryl sulfate were added to the reaction mixture. The mixture was incubated at 37° C. for 1 hour. After reaction, the mixture was subjected to phenol-chloroform extraction, ethanol precipitation and air-drying, and then dissolved in 50 µl of TE to obtain a genomic DNA solution.

(2) Cloning of RNase HII Gene

The entire genomic sequence of the *Archaeoglobus fulgidus* has been published [Klenk, HP et al., Nature, 390:364-370 (1997)]. The existence of one gene encoding a homologue of RNase HII (AF0621) was known (SEQ ID NO:33, www.tigr.org/tdb/CMR/btm/htmls/SplashPage.htlm).

Primers AfuNde (SEQ ID NO:34) and AfuBam (SEQ ID NO:35) were synthesized on the basis of the sequence of the AF0621 gene (SEQ ID NO:33).

A PCR was carried out using 30 ng of the *Archaeoglobus fulgidus* genomic DNA prepared in Example 7-(1) as a template, and 20 pmol each of AfuNde and AfuBam as primers in a volume of 100 µl. Pyrobest DNA polymerase (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.6 kb was digested with NdeI and BamHI (both from Takara Shuzo). Then, a plasmid pAFU204 was constructed by incorporating the resulting DNA fragment between NdeI and BamHI sites in a plasmid vector pTV119Nd (a plasmid in which the NcoI site in pTV119N is converted into a NdeI site).

(3) Determination of Nucleotide Sequence of DNA Fragment Containing RNase HII Gene The nucleotide sequence of the DNA fragment inserted into pAFU204 obtained in Example 7-(2) was determined according to a dideoxy method.

Analysis of the determined nucleotide sequence revealed an open reading frame presumably encoding RNase HII. The nucleotide sequence of the open reading frame is shown in SEQ ID NO:36. The amino acid sequence of RNase HII deduced from the nucleotide sequence is shown in SEQ ID NO:37.

*Escherichia coli* JM109 transformed with the plasmid pAFU204 is designated and indicated as *Escherichia coli* JM109/pAFU204, and deposited on Feb. 22, 2001 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7691.

(4) Preparation of Purified RNase HII Preparation

*Escherichia coli* JM109 was transformed with pAFU204 obtained in Example 7-(2). The resulting *Escherichia coli* JM109 harboring pAFU204 was inoculated into 2 L of LB medium containing 100 µg/ml of ampicillin and cultured with shaking at 37° C. for 16 hours. After cultivation, cells collected by centrifugation were suspended in 37.1 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12,000 rpm for 10 minutes was heated at 70° C. for 15 minutes. It was then centrifuged again at 12,000 rpm for 10 minutes to collect a supernatant. Thus, 40.3 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

The flow-through RNase HII fraction was subjected to RESOURSE S column (Amersham Pharmacia Biotech) equilibrated with Buffer A and chromatographed using FPLC system (Amersham Pharmacia Biotech). As a result, RNase HII flowed through the RESOURSE S column.

40.0 ml of the flow-through RNase HII fraction was dialyzed against 2 L of Buffer B (50 mM tris-HCl (pH 7.0), 1 mM EDTA) containing 50 mM NaCl for 2 hours. The dialysis was repeated two more times. 40.2 ml of the dialyzed enzyme solution was subjected to HiTrap-heparin column (Amersham Pharmacia Biotech) equilibrated with Buffer B containing 50 mM NaCl and eluted with a linear gradient of 50 to 550 mM NaCl using FPLC system. As a result, a fraction containing RNase HII eluted with about 240 mM NaCl was obtained.

7.8 ml of the RNase HII fraction was concentrated by ultrafiltration using Centricon-10 (Millipore). Four portions each separated from about 600 µl of the concentrate were subjected to Superose 6 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HII was eluted at a position corresponding to a molecular weight of 30.0 kilodalton. This molecular weight corresponds to that of the RNase HII in the monomeric form.

The RNase HII eluted as described above was used as Afu RNase HII preparation.

The enzymatic activity of the thus obtained Afu RNase HII preparation was measured as described in Example 3-(5). As a result, an RNase H activity was observed for the Afu RNase HII preparation.

Example 8

Cloning of *Thermococcus Litoralis* RNase HII Gene (1) Preparation of Genomic DNA from *Thermococcus litoralis*

*Thermococcus litoralis* (purchased from Deutsche Sammlung von Mikroorganismen und Zellkulturen GmbH;

DSM5473) cells were collected from 11 ml of culture. The cells were suspended in 500 µl of 25% sucrose and 50 mM tris-HCl (pH 8.0). 100 µl of 0.5 M EDTA and 50 µl of 10 mg/ml lysozyme chloride (Nacalai Tesque) in water were added thereto. The mixture was reacted at 20° C. for 1 hour. After reaction, 4 ml of a mixture containing 150 mM NaCl, 1 mM EDTA and 20 mM tris-HCl (pH 8.0), 50 µl of 20 mg/ml proteinase K (Takara Shuzo) and 250 µl of a 10% aqueous solution of sodium lauryl sulfate were added to the reaction mixture. The mixture was incubated at 37° C. for 1 hour. After reaction, the reaction was subjected to phenol-chloroform extraction and ethanol precipitation, air-dried and then dissolved in 100 µl of TE buffer to obtain a genomic DNA solution.

(2) Cloning of Middle Portion of RNase HII Gene

Oligonucleotides RN-F1 and RN-R0 represented by SEQ ID NOS:38 and 39 were synthesized on the basis of portions conserved among amino acid sequences of various thermostable RNase HIIs.

A PCR was carried out in a volume of 100 µl using 5 µl of the *Thermococcus litoralis* genomic DNA solution as prepared in Example 8-(1) as a template, and 100 pmol each of RN-F1 and RN-R0 as primers. TaKaRa Taq (Takara Shuzo) was used as a DNA polymerase for the PCR according to the attached protocol. The PCR was carried out as follows: 50 cycles of 94° C. for 30 seconds, 45° C. for 30 seconds and 72° C. for 1 minute. After reaction, Microcon-100 (Takara Shuzo) was used to remove primers from the reaction mixture and to concentrate the reaction mixture.

(3) Cloning of Upstream and Downstream Portions of RNase HII Gene

The nucleotide sequence of the inserted fragment of about 0.5 kb, TliF1R0, obtained in Example 8-(2) was determined. A specific oligonucleotide TliRN-1 (SEQ ID NO:40) for cloning the upstream portion and a specific oligonucleotide TliRN-2 (SEQ ID NO:41) for cloning the downstream portion were synthesized on the basis of the determined nucleotide sequence. In addition, 48 primers as shown in Table 1 were synthesized. The tag sequence in Table 1 is shown in SEQ ID NO:60.

TABLE 1

| No. | 5'-tag sequence-NN-SSSSSSS-3' (N: mixture of G, A, T and C; S represents the nucleotide sequence below) Nucleotide sequence |
|---|---|
| 1 | ggagcag |
| 2 | ggcaaag |
| 3 | ggcaacg |
| 4 | ggcacag |
| 5 | ggcattg |
| 6 | ggccaag |
| 7 | ggccttg |
| 8 | ggctaag |
| 9 | ggctacg |
| 10 | ggctcag |
| 11 | ggctttg |
| 12 | gggacag |
| 13 | gggcaag |
| 14 | gggcttg |
| 15 | gggtacg |
| 16 | ggtaacg |
| 17 | ggtacgg |
| 18 | ggtgcg |
| 19 | gtaacgg |
| 20 | gtaagcg |
| 21 | gtacacg |
| 22 | gtagacg |

TABLE 1-continued

| No. | 5'-tag sequence-NN-SSSSSSS-3' (N: mixture of G, A, T and C; S represents the nucleotide sequence below) Nucleotide sequence |
|---|---|
| 23 | gtagcgg |
| 24 | gtcaacg |
| 25 | gcaccag |
| 26 | gcagacg |
| 27 | gcagcag |
| 28 | gcatggg |
| 29 | gccaaag |
| 30 | gccacag |
| 31 | gccattg |
| 32 | gcccaag |
| 33 | gcccttg |
| 34 | gcctacg |
| 35 | gcctcag |
| 36 | gcctttg |
| 37 | gcgcaag |
| 38 | gcgcttg |
| 39 | gcggacg |
| 40 | gcgtaag |
| 41 | gctacgg |
| 42 | gctcacg |
| 43 | gctccag |
| 44 | gcttgcg |
| 45 | gcttggg |
| 46 | ggacacg |
| 47 | ggaccag |
| 48 | ggagacg |

PCRs were carried out in reaction mixtures containing 1 µl of the *Thermococcus litoralis* genomic DNA solution prepared in Example 8-(1) as a template, a combination of 20 pmol of TliRN-1 or 20 pmol of TliRN-2 and 20 pmol of one of the 48 primers listed in Table 1, 20 mM tris-acetate (pH 8.5), 50 mM potassium acetate, 3 mM magnesium acetate, 0.01% BSA, 30 µM each of dNTPs and 2.5 units of TaKaRa Ex Taq DNA polymerase (Takara Shuzo). PCRs were carried out as follows: incubation at 94° C. for 3 minutes; and 40 cycles of 98° C. for 10 seconds, 50° C. for 10 seconds and 72° C. for 40 seconds. A portion of each PCR product was subjected to agarose gel electrophoresis. Microcon-100 (Takara Shuzo) was used to remove primers from reaction mixtures that resulted in single bands and to concentrate the reaction mixtures. The concentrates were subjected to direct sequencing to screen for fragments containing the upstream or downstream portions of the RNase HII. As a result, it was shown that an about 450-bp PCR-amplified fragment TliN7 contained the upstream portion of the RNase HII gene and an about 600-bp PCR-amplified fragment TliC25 and an about 400-bp PCR-amplified fragment TliC26 contained the downstream portion of the RNase HII gene, respectively.

(4) Cloning of Entire RNase HII Gene

The nucleotide sequence of a gene containing Tli RNase HII is shown in SEQ ID NO:42. The amino acid sequence of RNase HII deduced from the nucleotide sequence is shown in SEQ ID NO:43. Primers TliNde (SEQ ID NO:44) and TliBam (SEQ ID NO:45) were synthesized on the basis of the nucleotide sequence.

A PCR was carried out in a volume of 100 µl using 1 µl of the *Thermococcus litoralis* genomic DNA solution as prepared in Example 8-(1) as a template, and 20 pmol each of TliNde and TliBam as primers. Ex Taq DNA polymerase (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.7 kb was digested with NdeI and BamHI (both from Takara Shuzo). Then, plasmids pTLI223Nd and pTLI204 were constructed by incorporating the resulting DNA fragment between NdeI and BamHI sites in a plasmid vector pTV119Nd (a plasmid in which the NcoI site in pTV119N is converted into a NdeI site) or pET3a (Novagen), respectively.

(5) Determination of Nucleotide Sequence of DNA Fragment Containing RNase HII Gene The nucleotide sequences of the DNA fragments inserted into pTLI223Nd and pTLI204 obtained in Example 8-(4) were determined according to a dideoxy method.

Analyses of the determined nucleotide sequences revealed the existence of open reading frames each presumably encoding RNase HII. The nucleotide sequence of the open reading frame in pTLI204 is shown in SEQ ID NO:46. The amino acid sequence of RNase HII deduced from the nucleotide sequence is shown in SEQ ID NO:47. "T" at position 484 in the nucleotide sequence of the open reading frame in pTLI204 was replaced by "C" in the nucleotide sequence of the open reading frame in pTLI223Nd. In the amino acid sequence, phenylalanine at position 162 was replaced by leucine.

*Escherichia coli* HMS174(DE3) transformed with the plasmid pTLI204 is designated and indicated as *Escherichia coli* HMS174(DE3)/pTLI204, and deposited on Feb. 22, 2001 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7693.

(6) Expression of *Thermococcus litoralis* RNase HII Gene

*Escherichia coli* JM109 transformed with pTLI223Nd was inoculated into 10 ml of LB medium containing 100 pg/ml of ampicillin and 1 mM IPTG and cultured with shaking at 37° C. overnight. After cultivation, cells collected by centrifugation were suspended in 196 µl of Buffer A and sonicated. A supernatant obtained by centrifuging the sonicated suspension at 12,000 rpm for 10 minutes was heated at 70° C. for 10 minutes and then centrifuged again at 12,000 rpm for 10 minutes to collect a supernatant as a heated supernatant. Similarly, *Escherichia coli* HMS174(DE3) transformed with pTLI204 was inoculated into 10 ml of LB medium containing 100 µg/ml of ampicillin and cultured with shaking at 37° C. overnight. After cultivation, cells collected by centrifugation were processed according to the procedure as described above to obtain a heated supernatant.

The enzymatic activities were measured for the heated supernatants as described in Example 3-(5). As a result, RNase H activities were observed for both transformants. Thus, the activity of the polypeptide of the present invention was confirmed in spite of substitution in the nucleotide sequence or the amino acid sequence.

(7) Preparation of Purified RNase HII Preparation

*Escherichia coli* JM109 transformed with pTLI223Nd obtained in Example 8-(4) was inoculated into 2 L of LB medium containing 100 µg/ml of ampicillin and cultured with shaking at 37° C. for 16 hours. After cultivation, cells collected by centrifugation were suspended in 38.7 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12,000 rpm for 10 minutes was heated at 70° C. for 15 minutes. It was then centrifuged again at 12,000 rpm for 20 minutes to collect a supernatant. Thus, 37.2 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

The sample was subjected to RESOURSE S column (Amersham Pharmacia Biotech) equilibrated with Buffer A and eluted with a linear gradient of 0 to 500 mM NaCl using FPLC system (Amersham Pharmacia Biotech). A fraction containing RNase HII eluted with about 220 mM NaCl was obtained.

A mixture containing 3 ml of the RNase HII fraction and Buffer A added to make the NaCl concentration to 50 mM was subjected to HiTrap-heparin column (Amersham Pharmacia Biotech) equilibrated with Buffer A containing 50 mM NaCl and eluted with a linear gradient of 50 to 550 mM NaCl using FPLC system. As a result, a fraction containing RNase HII eluted with about 320 mM NaCl was obtained.

6 ml of the RNase HII fraction was concentrated by ultrafiltration using Centricon-10 (Millipore). About 198 µl of the concentrate was subjected to Superose 6 gel filtration column (Amersham Pharmacia Biotech) equilibrated with 50 mM tris-HCl (pH 8.0) containing 100 mM NaCl and 0.1 mM EDTA and eluted with the same buffer. As a result, RNase HII was eluted at a position corresponding to a molecular weight of 26.5 kilodalton. This molecular weight corresponds to that of the RNase HII in the monomeric form. The thus eluted RNase HII was used as Tli RNase HII preparation.

The enzymatic activity of the thus obtained Tli RNase HII preparation was measured as described in Example 3-(5). As a result, an RNase H activity was observed for the Tli RNase HII preparation.

Example 9

Cloning of *Thermococcus celer* RNase HII Gene (1) Preparation of Genomic DNA from *Thermococcus celer*

*Thermococcus celer* (purchased from Deutsche Sammlung von Mikroorganismen und Zellkulturen GmbH; DSM2476) cells were collected from 11 ml of culture. A genomic DNA solution was obtained as described in Example 8-(1).

(2) Cloning of Middle Portion of RNase HII Gene

Oligonucleotides RN-F1 and RN-R0 represented by SEQ ID NOS:48 and 49 were synthesized on the basis of portions conserved among amino acid sequences of various thermostable RNase HIIs.

A PCR was carried out in a volume of 100 µl using 5 µl of the *Thermococcus celer* genomic DNA solution as prepared in Example 9-(1) as a template, and 100 pmol each of RN-F1 and RN-R0 as primers. TaKaRa Taq (Takara Shuzo) was used as a DNA polymerase for the PCR according to the attached protocol. The PCR was carried out as follows: 50 cycles of 94° C. for 30 seconds, 45° C. for 30 seconds and 72° C. for 1 minute. After reaction, an about 500-bp DNA fragment obtained by amplification was blunt-ended using T4 DNA polymerase (Takara Shuzo) and then subjected to agarose gel electrophoresis to recover an amplified DNA fragment of about 500 bp. The about 500-bp DNA fragment was ligated with pUC119 (Takara Shuzo) digested with SmaI (Takara Shuzo) using T4 DNA ligase (Takara Shuzo). The ligation mixture was used to transform *Escherichia coli* JM109.

The resulting transformants were cultured to obtain a plasmid pTceF1R0 into which the about 500-bp DNA fragment was inserted.

(3) Cloning of Upstream and Downstream Portions of RNase HII Gene

The nucleotide sequence of the plasmid pTceF1R0 obtained in Example 9-(2) was determined. A specific oligonucleotide TceRN-1 (SEQ ID NO:50) for cloning the upstream portion and a specific oligonucleotide TceRN-2 (SEQ ID NO:51) for cloning the downstream portion were synthesized on the basis of the determined nucleotide sequence.

PCRs were carried out in reaction mixtures containing 1 µl of the *Thermococcus celer* genomic DNA solution prepared in Example 9-(1) as a template, a combination of 20 pmol of TliRN-1 or 20 pmol of TliRN-2 and 20 pmol of one of the 48 primers (listed in Table 1, Example 8), 20 mM tris-acetate (pH 8.5), 50 mM potassium acetate, 3 mM magnesium acetate, 0.01% BSA, 30 µM each of dNTPs and 2.5 units of TaKaRa Ex Taq DNA polymerase (Takara Shuzo). PCRs were carried out as follows: incubation at 94° C. for 3 minutes; and 40 cycles of 98° C. for 10 seconds, 50° C. for 10 seconds and 72° C. for 40 seconds. Microcon-100 (Takara Shuzo) was used to remove primers from reaction mixtures that resulted in single bands for the PCR products and to concentrate the reaction mixtures. The concentrates were subjected to direct sequencing to screen for fragments containing the upstream or downstream portion of the RNase HII. As a result, it was shown that an about 450-bp PCR-amplified fragment TceN24 contained the upstream portion of the RNase HII gene and an about 400-bp PCR-amplified fragment TceC29 contained the downstream portion of the RNase HII gene, respectively.

(4) Cloning of Entire RNase HII Gene

The nucleotide sequence of a gene containing Tce RNase HII is shown in SEQ ID NO:52. The amino acid sequence of RNase HII deduced from the nucleotide sequence is shown in SEQ ID NO:53. Primers TceNde (SEQ ID NO:54) and TceBam (SEQ ID NO:55) were synthesized on the basis of the nucleotide sequence.

A PCR was carried out in a volume of 100 µl using 1 µl of the *Thermococcus celer* genomic DNA solution as prepared in Example 9-(1) as a template, and 20 pmol each of TceNde and TceBam as primers. Pyrobest DNA polymerase (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.7 kb was digested with NdeI and BamHI (both from Takara Shuzo). Then, plasmids pTCE265Nd and pTCE207 were constructed by incorporating the resulting DNA fragment between NdeI and BamHI sites in a plasmid vector pTV119Nd (a plasmid in which the NcoI site in pTV119N is converted into a NdeI site) or pET3a (Novagen), respectively.

(5) Determination of Nucleotide Sequence of DNA Fragment Containing RNase HII Gene The nucleotide sequences of the DNA fragments inserted into pTCE265Nd and pTCE207 obtained in Example 9-(4) were determined according to a dideoxy method.

Analyses of the determined nucleotide sequences revealed the existence of open reading frames each presumably encoding RNase HII. The nucleotide sequence of the open reading frame in pTCE207 is shown in SEQ ID NO:56. The amino acid sequence of RNase HII deduced from the nucleotide sequence is shown in SEQ ID NO:57. "A" at position 14 in the nucleotide sequence of the open reading frame in pTCE207 was replaced by "G" in the nucleotide sequence of the open reading frame in pTCE265Nd and nucleotides at positions 693 to 696 were deleted. As a result, glutamic acid at position 5 was replaced by glycine and phenylalanine at position 231 was missing in the amino acid sequence.

*Escherichia coli* HMS174(DE3) transformed with the plasmid pTCE207 is designated and indicated as *Escherichia coli* HMS174(DE3)/pTCE207, and deposited on Feb. 22, 2001 (date of original deposit) at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM BP-7694.

(6) Expression of *Thermococcus celer* RNase HII Gene

*Escherichia coli* JM109 transformed with pTCE265Nd was inoculated into 10 ml of LB medium containing 100 µg/ml of ampicillin and 1 mM IPTG and cultured with shaking at 37° C. overnight. After cultivation, cells collected by centrifugation were suspended in 203 µl of Buffer A and sonicated. A supernatant obtained by centrifuging the sonicated suspension at 12,000 rpm for 10 minutes was heated at 70° C. for 10 minutes and then centrifuged again at 12,000 rpm for 10 minutes to collect a supernatant as a heated supernatant. Similarly, *Escherichia coli* HMS174(DE3) transformed with pTCE207 was inoculated into 10 ml of LB medium containing 100 µg/ml of ampicillin and cultured with shaking at 37° C. overnight. After cultivation, cells collected by centrifugation were processed according to the procedure as described above to obtain a heated supernatant.

The enzymatic activities were measured for the heated supernatants as described in Example 3-(5). As a result, RNase H activities were observed for both transformants. Thus, the activity of the polypeptide of the present invention was confirmed in spite of substitution and deletion in the nucleotide sequence or the amino acid sequence.

(7) Preparation of Purified RNase HII Preparation

*Escherichia coli* JM109 transformed with pTCE265Nd obtained in Example 9-(4) was inoculated into 2 L of LB medium containing 100 µg/ml of ampicillin and cultured with shaking at 37° C. for 16 hours. After cultivation, cells collected by centrifugation were suspended in 39 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12,000 rpm for 10 minutes was heated at 70° C. for 15 minutes. It was then centrifuged again at 12,000 rpm for 20 minutes to collect a supernatant. Thus, 37.5 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

The sample was subjected to RESOURSE S column (Amersham Pharmacia Biotech) equilibrated with Buffer A and eluted with a linear gradient of 0 to 500 mM NaCl using FPLC system (Amersham Pharmacia Biotech). As a result, a fraction containing RNase HII eluted with about 220 mM NaCl was obtained.

A mixture containing 3 ml of the RNase HII fraction and Buffer A added to make the NaCl concentration to 50 mM was subjected to HiTrap-heparin column (Amersham Pharmacia Biotech) equilibrated with Buffer A containing 50 mM NaCl and eluted with a linear gradient of 50 to 550 mM NaCl using FPLC system. As a result, a fraction containing RNase HII eluted with about 415 mM NaCl was obtained.

6 ml of the RNase HII fraction was concentrated by ultrafiltration using Centricon-10. About 178 µl of the concentrate was subjected to Superose 6 gel filtration column (Amersham Pharmacia Biotech) equilibrated with 50 mM tris-HCl (pH 8.0) containing 100 mM NaCl and 0.1 mM EDTA and eluted with the same buffer. As a result, RNase HII was eluted at a position corresponding to a molecular weight of 29.5 kilodalton. This molecular weight corresponds to that of the RNase HII in the monomeric form. The thus eluted RNase HII was used as Tce RNase HII preparation.

The enzymatic activity of the thus obtained Tce RNase HII preparation was measured as described in Example 3-(5). As a result, an RNase H activity was observed for the Tce RNase HII preparation.

Example 10

Homology searches were conducted for the amino acid sequences and nucleotide sequences from *Bacillus caldotenax* (hereinafter referred to as BCA), *Pyrococcus furiosus* (PFU), *Thermotoga maritima* (TMA), *Archaeoglobus fulgidus* (AFU), *Thermococcus litoralis* (TLI), *Thermococcus celer* (TCE) and *Pyrococcus horikoshii* (PHO) obtained in Examples 2 to 9. Calculation was conducted using Maximum Matching in DNASIS-Mac (Takara Shuzo) or a computer algorithm FASTA (version 3.0; Pearson, W. R. et al., Pro. Natl. Acad. Sci., 85:2444-2448, 1988) as a search program.

Homologies of the PFU amino acid sequence to the PHO, AFU, TLI and TCE amino acid sequences as determined using DNASIS were 69%, 45%, 65% and 58%, respectively. Homologies of the PFU nucleotide sequence to the PHO, AFU, TLI and TCE nucleotide sequences as determined using DNASIS were 68%, 60%, 65% and 61%, respectively.

Gene database searches were conducted for PHO, AFU and TMA using the computer algorithm FASTA. For the PHO amino acid sequence, the highest homology to an amino acid sequence presumed to be of a ribonuclease was 70% and the lowest was 20%. The homology of PHO to AFU was 50% and the homology of PHO to TMA was 35%. For the AFU amino acid sequence, the highest homology was 50% and the lowest was 25%. The amino acid sequence homology of AFU to TMA was 32%. For the TMA amino acid sequence, the highest homology was 52% and the lowest was 22%.

Gene database searches were conducted for BCA, PFU, TCE and TLI using the computer algorithm BLAST. For the BCA ribonuclease HII, BCA ribonuclease HIII, PFU, TCE and TLI amino acid sequences, the highest homologies to amino acid sequences presumed to be of ribonucleases were 43%, 46%, 68%, 70% and 64%, respectively.

In addition, the amino acid sequence homology of PHO to AFU as determined using DNASIS was also 50%. The value determined using the computer algorithm FASTA was 50% as described above. Thus, it was shown that there was no significant difference between homology values obtained using DNASIS and the computer algorithm FASTA.

Example 11

Modes of Action and Properties of Various RNase Hs
(1) Mode of Action of Bca RNase HIII A substrate was prepared as follows in order to compare the fashions of cleavage of Bca RNase HIII and *E. coli* RNase HI. A PCR was carried out using a heat extract of *Escherichia coli* O157 as a template, a 5' FITC-labeled chimeric primer VT2-R280N3-17 (SEQ ID NO:61) in which three nucleotides from the 3' end are RNAs, and a DNA primer VT2-F110 (SEQ ID NO:62) to obtain a DNA fragment having three RNAs in one of the two strands. Microcon-100 (Millipore) was used to remove primers from the PCR product to obtain a substrate for cleavage with RNase H.

39.2 µl of a reaction buffer (20 mM Hepes-KOH (pH 7.8), 1% dimethyl sulfoxide, 0.01% bovine serum albumin, 100 mM potassium acetate, 4 mM magnesium acetate, 0.002% propyrenediamine) containing 0.3 pmol of the substrate was prepared. 0.8 µl of *E. coli* RNase HI 30 U/µl (Takara Shuzo) or a 10-fold dilution of the purified preparation of Bca RNase HIII obtained in Example 3-(5) with Buffer A was added thereto. The mixtures were reacted at 55° C. for 5 or 10 minutes. After reaction, 2 µl each of the reaction mixtures was subjected to electrophoresis on denaturing 10% acrylamide gel to determined the sizes of cleaved DNA fragments.

In case of *E. coli* RNase HI, signals appeared at positions of 18 bases and 19 bases. The signal at the position of 19 bases decreased over time. Background at a position of 20 bases due to incomplete removal of primers also decreased over time. In case of Bca RNase HIII, a signal appeared at a position of 19 bases. No decrease in primer background was observed.

Based on the above, *E. coli* RNase HI cleaves at two sites between RNAs. In addition, it was considered that *E. coli* RNase HI had an activity of cleaving on the 5' side of a 3' RNA and further cleaving on the 5' side of a 3' RNA which was not attached to a DNA. On the other hand, it was considered that Bca RNase HIII only cleaved on the 5' side of a 3' RNA and did not cleave if DNA was not attached on the 3' side of an RNA. Thus, it was considered that the cleavage site selectivity of Bca RNase HIII was higher than that of *E. coli* RNase HI.

(2) Modes of Action of Pfu RNase HII, Pho RNase HII and Afu RNase HII

Substrates were prepared as follows in order to analyze the fashions of cleavage of Pfu (*Pyrococcus furiosus*) RNase HII, Pho (*Pyrococcus horikoshii*) RNase HII and Afu (*Archaeoglobus fulgidus*) RNase HII. PCRs were carried out using a heat extract of *Escherichia coli* O157 as a template, a 5' FITC-labeled chimeric primer VT2-IF20N3 (SEQ ID NO:63) in which three nucleotides from the 3' end are RNAs, a 5° FITC-labeled chimeric primer VT2-IF19N2 (SEQ ID NO:64) in which two nucleotides from the 3' end are RNAs or a 5° FITC-labeled chimeric primer VT2-IF18N1 (SEQ ID NO:65) in which one nucleotide at the 3' end is RNA, and a DNA primer VT21R20 (SEQ ID NO:66) to obtain DNA fragments VFN3, VFN2 and VFN1 which had three, two and one RNA(s) in one of the two strands, respectively. Microcon-100 was used to remove primers from the PCR products to obtain substrates for cleavage with RNase H.

39 µl of a reaction buffer (20 mM Hepes-KOH (pH 7.8), 1% dimethyl sulfoxide, 0.01% bovine serum albumin, 100 mM potassium acetate, 4 mM magnesium acetate, 0.002% propyrenediamine) containing 0.3 pmol of one of the substrates was prepared. 1 µl of one of the purified preparations of the respective RNase Hs at a concentration of 37.2 U/µl was added thereto. The mixtures were reacted at 55° C. for 5 or 10 minutes. After reaction, 2 µl each of the reaction mixtures was subjected to electrophoresis on denaturing 10% acrylamide gel to determined the sizes of cleaved DNA fragments.

For each of Pfu RNase HII, Pho RNase HII and Afu RNase HII, a signal was observed at a position of 19 bases using VFN3 as a substrate. For each of Pfu RNase HII, Pho RNase HII and Afu RNase HII, a signal was observed at a position of 18 bases using VFN2 as a substrate. For each of Pfu RNase HII and Pho RNase HII, a signal was observed at a position of 17 bases using VFN1 as a substrate.

Based on the above, Pfu RNase HII, Pho RNase HII and Afu RNase HII cleaved on the 5' side of a 3' RNA. Pfu RNase HII and Pho RNase HII cleaved on the 5' side of an RNA even if the number of RNA was one. There has been no report on an RNase H that cleaves even if the number of RNA is one. Since the intensities of the signals upon cleavage were similar regardless of the number of RNAs, it was shown that there was no difference in cleavage efficiency depending on the number of RNAs. In addition, since decrease in an appeared signal over time or appearance of a shorter signal was not observed, it was shown that no cleavage takes place if DNA was not attached on the 3' side of an RNA.

(3) Ion Requirements of Bca RNase HII and Tma RNase HII

According to the method for measuring an RNase H activity as described in Example 1, Bca RNase HII and Tma RNase HII required $Mn^{2+}$ and did not exhibit an activity in the presence of $Mg^{2+}$ at all. Comparison of cleavage in the presence of $Mg^{2+}$ or $Mn^{2+}$ was carried out using VFN3 as described in Example 11-(2) as a substrate for them.

39.2 µl of a reaction buffer (20 mM Hepes-KOH (pH 7.8), 1% dimethyl sulfoxide, 0.01% bovine serum albumin, 100 mM potassium acetate, 4 mM magnesium acetate, 0.002% propyrenediamine) containing 0.3 pmol of the substrate and 39.2 µl of a Mn+ reaction buffer (20 mM Hepes-KOH (pH 7.8), 1% dimethyl sulfoxide, 0.01% bovine serum albumin, 100 mM potassium acetate, 10 mM manganese chloride, 0.002% propyrenediamine) containing 0.3 pmol of the substrate were prepared. 0.8 µl of *E. coli* RNase HI (30 U/µl; Takara Shuzo), a 10-fold dilution of the purified preparation of Bca RNase HII (obtained in Example 2-(6)) with Buffer A or a 25-fold dilution of the crude cell extract of Tma RNase HII (obtained in Example 5-(3)) with Buffer A was added thereto. The mixtures were reacted at 55° C. for 5 or 10 minutes. After reaction, 2 µl each of the reaction mixtures was subjected to electrophoresis on denaturing 10% acrylamide gel to determined the sizes of cleaved DNA fragments.

When Bca RNase HII or Tma RNase HII was used in the presence of $Mg^{2+}$ or $Mn^{2+}$, a signal appeared at a position of 19 bases in each case. The levels of the signals were equivalent each other.

Bca RNase HII and Tma RNase HII did not exhibit an activity in the presence of $Mg^{2+}$ at all according to the method for measuring an RNase H activity as described in Example 1. However, they exhibited cleavage activities in the presence of $Mg^{2+}$ which were equivalent to those observed in the presence of $Mn^{2+}$ as described above.

Base on the above, it was shown that the enzymes may not require $Mn^{2+}$ for cleavage depending on the form of a substrate, it may be possible to substitute $Mg^{2+}$ for $Mn^{2+}$, and a reaction in the same reaction mixture for an enzyme that requires $Mn^{2+}$ or $Mg^{2+}$ may be possible.

(4) Examination of Thermostability of RNase H

Thermostabilities were examined using *Escherichia coli* transformed with the following: pRHB11 and pBCA3Nd obtained in Examples 2-(5) and 3-(4) for *Bacillus caldotenax* RNase H; pPFU220 obtained in Example 4-(2) for *Pyrococcus furiosus* RNase H; pTM-RNH obtained in Example 5-(2) for *Thermotoga maritima* RNase H; pPHO238 obtained in Example 6-(2) for *Pyrococcus horikoshii* RNase H; pAFU204 obtained in Example 7-(2) for *Archaeoglobus fulgidus* RNase H; pTLI204 and pTLI223Nd obtained Example 8-(4) for *Thermococcus litoralis* RNase H; and pTCE207 and pTCE265Nd obtained in Example 9-(4) for *Thermococcus celer* RNase H. The *E. coli* strains were cultured, crude enzyme extracts prepared from the cultures were heated at 60° C. for 15 minutes, and the RNase H activities were determined according to the method as described in Example 1. As a result, RNase H activities were observed for the RNase Hs from all of the strains.

INDUSTRIAL APPLICABILITY

The present invention provides a polypeptide having an RNase H activity which is highly valuable for genetic engineering, a gene encoding said polypeptide and a method for producing said polypeptide by genetic engineering. Since the RNase H of the present invention is thermostable, the present invention provide a method for producing an RNase H which is industrially advantageous.

It is now possible to use the RNase H of the present invention for various uses according to the present invention.

Sequence Listing Free Text

SEQ ID NO:1: PCR primer BsuII-3 for cloning a gene encoding a polypeptide having a RNase HII activity from *Bacillus caldotenax*.

SEQ ID NO:2: PCR primer BsuII-6 for cloning a gene encoding a polypeptide having a RNase HII activity from *Bacillus caldotenax*.

SEQ ID NO:3: PCR primer RNII-S1 for cloning a gene encoding a polypeptide having a RNase HII activity from *Bacillus caldotenax*.

SEQ ID NO:4: PCR primer RNII-S2 for cloning a gene encoding a polypeptide having a RNase HII activity from *Bacillus caldotenax*.

SEQ ID NO:5: PCR primer RNII-S5 for cloning a gene encoding a polypeptide having a RNase HII activity from *Bacillus caldotenax*.

SEQ ID NO:6: PCR primer RNII-S6 for cloning a gene encoding a polypeptide having a RNase HII activity from *Bacillus caldotenax*.

SEQ ID NO:7: PCR primer RNII-Nde for cloning a gene encoding a polypeptide having a RNase HII activity from *Bacillus caldotenax*.

SEQ ID NO:10: PCR primer BsuIII-1 for cloning a gene encoding a polypeptide having a RNase HIII activity from *Bacillus caldotenax*.

SEQ ID NO:11: PCR primer BsuIII-3 for cloning a gene encoding a polypeptide having a RNase HIII activity from *Bacillus caldotenax*.

SEQ ID NO:12: PCR primer BsuIII-6 for cloning a gene encoding a polypeptide having a RNase HIII activity from *Bacillus caldotenax*.

SEQ ID NO:13: PCR primer BsuIII-8 for cloning a gene encoding a polypeptide having a RNase HIII activity from *Bacillus caldotenax*.

SEQ ID NO:14: PCR primer RNII1-S3 for cloning a gene encoding a polypeptide having a RNase HIII activity from *Bacillus caldotenax*.

SEQ ID NO:15: PCR primer BcaRNIII-3 for cloning a gene encoding a polypeptide having a RNase HIII activity from *Bacillus caldotenax*.

SEQ ID NO:18: PCR primer BcaRNIIINde for amplifying a gene encoding a polypeptide having a RNase HIII activity from *Bacillus caldotenax*.

SEQ ID NO:20: PCR primer 1650Nde for cloning a gene encoding a polypeptide having a RNase HII activity from *Pyrococcus furiosus*.

SEQ ID NO:21: PCR primer 1650Bam for cloning a gene encoding a polypeptide having a RNase HII activity from *Pyrococcus furiosus*.

SEQ ID NO:24: PCR primer 915-F1 for cloning a gene encoding a polypeptide having a RNase HII activity from *Thermotoga maritima*.

SEQ ID NO:25: PCR primer 915-F2 for cloning a gene encoding a polypeptide having a RNase HII activity from *Thermotoga maritima*.

SEQ ID NO:26: PCR primer 915-R1 for cloning a gene encoding a polypeptide having a RNase HII activity from *Thermotoga maritima*.

SEQ ID NO:27: PCR primer 915-R2 for cloning a gene encoding a polypeptide having a RNase HII activity from *Thermotoga maritima*.

SEQ ID NO:29: PCR primer PhoNde for cloning a gene encoding a polypeptide having a RNase HII activity from *Pyrococcus horikoshii*.

SEQ ID NO:30: PCR primer PhoBam for cloning a gene encoding a polypeptide having a RNase HII activity from *Pyrococcus horikoshii*.

SEQ ID NO:34: PCR primer AfuNde for cloning a gene encoding a polypeptide having a RNase HII activity from *Archaeoglobus fulgidus*.

SEQ ID NO:35: PCR primer AfuBam for cloning a gene encoding a polypeptide having a RNase HII activity from *Archaeoglobus fulgidus*.

SEQ ID NO:38: PCR primer RN-F1 for cloning a gene encoding a polypeptide having a RNase HII activity from *Thermococcus litoralis*.

SEQ ID NO:39: PCR primer RN-R0 for cloning a gene encoding a polypeptide having a RNase HII activity from *Thermococcus litoralis*.

SEQ ID NO:40: PCR primer TliRN-1 for cloning a gene encoding a polypeptide having a RNase HII activity from *Thermococcus litoralis*.

SEQ ID NO:41: PCR primer TliRN-2 for cloning a gene encoding a polypeptide having a RNase HII activity from *Thermococcus litoralis*.

SEQ ID NO:44: PCR primer TliNde for amplifying a gene encoding a polypeptide having a RNase HII activity from *Thermococcus litoralis*.

SEQ ID NO:45: PCR primer TliBam for amplifying a gene encoding a polypeptide having a RNase HIII activity from *Thermococcus litoralis*.

SEQ ID NO:48: PCR primer RN-F1 for cloning a gene encoding a polypeptide having a RNase HII activity from *Thermococcus celer*.

SEQ ID NO:49: PCR primer RN-R0 for cloning a gene encoding a polypeptide having a RNase HII activity from *Thermococcus celer*.

SEQ ID NO:50: PCR primer TceRN-1 for cloning a gene encoding a polypeptide having a RNase HII activity from *Thermococcus celer*.

SEQ ID NO:51: PCR primer TceRN-2 for cloning a gene encoding a polypeptide having a RNase HII activity from *Thermococcus celer*.

SEQ ID NO:54: PCR primer TceNde for amplifying a gene encoding a polypeptide having a RNase HII activity from *Thermococcus celer*.

SEQ ID NO:55: PCR primer TceBam for amplifying a gene encoding a polypeptide having a RNase HIII activity from *Thermococcus celer*.

SEQ ID NO:61: Designed chimeric oligonucleotide primer as VT2-R280N3-17 for amplifying a portion of vero tox in 2-encoding sequence from hemorrhagic *Escherichia coli* 0-157. “Nucleotides 18 to 20 are ribonucleotides-other nucleotides are deoxyribonucleotides”

SEQ ID NO:62: Designed oligonucleotide primer as VT2-F110 for amplifying a portion of vero toxin 2-encoding sequence from hemorrhagic *Escherichia coli* 0-157.

SEQ ID NO:63: Designed chimeric oligonucleotide primer as VT2-IF20N3 for amplifying a VFN3 from hemorrhagic *Escherichia coli* 0-157. “Nucleotides 17 to 19 are ribonucleotides-other nucleotides are deoxyribonucleotides”

SEQ ID NO:64: Designed chimeric oligonucleotide primer as VT2-IF19N2 for amplifying VFN2 from hemorrhagic *Escherichia coli* 0-157. “Nucleotides 16 to 18 are ribonucleotides-other nucleotides are deoxyribonucleotides”

SEQ ID NO:65: Designed chimeric oligonucleotide primer as VT2-IF18N1 for amplifying a VFN1 from hemorrhagic *Escherichia coli* 0-157. “Nucleotides 15 to 17 are ribonucleotides-other nucleotides are deoxyribonucleotides”

SEQ ID NO:66: Designed oligonucleotide primer as VT21R20 for amplifying a portion of vero toxin 2-encoding sequence from hemorrhagic *Escherichia coli* 0-157.

The invention claimed is:

1. An isolated and purified polypeptide having thermostable ribonuclease H activity, which is encoded by the plasmid pTLI204 (FERM BP-7693).

2. An isolated and purified polypeptide, comprising the amino acid sequence of SEQ ID NO:47 and having thermostable ribonuclease H activity.

* * * * *

SEQUENCE LISTING

```
<160> NUMBER OF SEQ ID NOS: 66

<210> SEQ ID NO 1
<211> LENGTH: 20
<212> TYPE: DNA
<213> ORGANISM: Artificial
<220> FEATURE:
<223> OTHER INFORMATION: PCR primer BsuII-3 for cloning a gene encoding
      a polypeptide having a RNaseHII activity from Bacillus caldotenax
<220> FEATURE:
<221> NAME/KEY: misc_feature
<222> LOCATION: (15)..(15)
<223> OTHER INFORMATION: n is a, c, g, or t

<400> SEQUENCE: 1
gtcgccagcg cagtnathyt                                                20

<210> SEQ ID NO 2
<211> LENGTH: 20
<212> TYPE: DNA
<213> ORGANISM: Artificial
<220> FEATURE:
<223> OTHER INFORMATION: PCR primer BsuII-6 for cloning a gene encoding
      a polypeptide having a RNaseHII activity from Bacillus caldotenax
```

```
<220> FEATURE:
<221> NAME/KEY: misc_feature
<222> LOCATION: (18)..(18)
<223> OTHER INFORMATION: n is a, c, g, or t

<400> SEQUENCE: 2
cggtccctcg tcacyttngc                                                   20

<210> SEQ ID NO 3
<211> LENGTH: 20
<212> TYPE: DNA
<213> ORGANISM: Artificial
<220> FEATURE:
<223> OTHER INFORMATION: PCR primer RNII-S1 for cloning a gene encoding
      a polypeptide having a RNaseHII activity from Bacillus caldotenax

<400> SEQUENCE: 3
cgcgcttttc cggcgtcagc                                                   20

<210> SEQ ID NO 4
<211> LENGTH: 20
<212> TYPE: DNA
<213> ORGANISM: Artificial
<220> FEATURE:
<223> OTHER INFORMATION: PCR primer RNII-S2 for cloning a gene encoding
      a polypeptide having a RNaseHII activity from Bacillus caldotenax

<400> SEQUENCE: 4
acggcgcacg cttcaatttg                                                   20

<210> SEQ ID NO 5
<211> LENGTH: 20
<212> TYPE: DNA
<213> ORGANISM: Artificial
<220> FEATURE:
<223> OTHER INFORMATION: PCR primer RNII-S5 for cloning a gene encoding
      a polypeptide having a RNaseHII activity from Bacillus caldotenax

<400> SEQUENCE: 5
acgcctattt gccggggctt                                                   20

<210> SEQ ID NO 6
<211> LENGTH: 20
<212> TYPE: DNA
<213> ORGANISM: Artificial
<220> FEATURE:
<223> OTHER INFORMATION: PCR primer RNII-S6 for cloning a gene encoding
      a polypeptide having a RNaseHII activity from Bacillus caldotenax

<400> SEQUENCE: 6
atgaccgacg cagcggcgat                                                   20

<210> SEQ ID NO 7
<211> LENGTH: 39
<212> TYPE: DNA
<213> ORGANISM: Artificial
<220> FEATURE:
<223> OTHER INFORMATION: PCR primer RNII-Nde for cloning a gene encoding
      a polypeptide having a RNaseHII activity from Bacillus caldotenax

<400> SEQUENCE: 7
tagaagaggg agaggcatat gaagcggtat acggtgaaa                              39

<210> SEQ ID NO 8
<211> LENGTH: 780
<212> TYPE: DNA
<213> ORGANISM: Bacillus caldotenax
```

<400> SEQUENCE: 8

```
atgaagcggt atacggtgaa agacattgaa gcgctgcttc gaagcttggg cgcggacgac    60
ccgcgctggg agatgctgcg gcaggatgag cgaaaaagcg tgcaggcgct tcttgcccgt   120
tttgaaaggc agaaagcgcg ccggcacgcc atcgagcagc ggtgggaaga actaatgcgt   180
tatgagaggg aactatacgc cgctggcgtt agacggatcg ccggcattga tgaggccggg   240
cgcggcccgc tggccggccc ggtcgtcgcc gccgcggtca tcttgccgaa agacgcctat   300
ttgccggggc ttgacgactc gaagcggctg acgccggaaa agcgcgaggc attgtttgcg   360
caaattgaag cgtgcgccgt cgccatcggc atcggcatcg tcagcgcggc ggagatcgat   420
gaaaggaata tttacgaagc gacaaggcaa gcgatggcga aagcggtgaa cgcccttccc   480
ccgccgcctg aacatttgct tgttgatgcg atggcggtgc cgtgcccact gccgcaacag   540
cgcctcataa aggagacgc caacagcgct tcaatcgccg ctgcgtcggt catcgccaaa   600
gtgacgcgcg accggtggat gaaagaactg gatcgccgct atccacaata cgggttcgcg   660
cgccatatgg gctacggaac gccggaacat ttcgaggcga tccgccgcta cggcgttacg   720
cctgagcacc gtcgttcgtt cgcaccggtg agggaggtgc tgaaggcgag cgagcagctc   780
```

<210> SEQ ID NO 9
<211> LENGTH: 260
<212> TYPE: PRT
<213> ORGANISM: Bacillus caldotenax

<400> SEQUENCE: 9

```
Met Lys Arg Tyr Thr Val Lys Asp Ile Glu Ala Leu Leu Pro Lys Leu
1               5                   10                  15

Gly Ala Asp Asp Pro Arg Trp Glu Met Leu Arg Gln Asp Glu Arg Lys
            20                  25                  30

Ser Val Gln Ala Leu Leu Ala Arg Phe Glu Arg Gln Lys Ala Arg Arg
        35                  40                  45

His Ala Ile Glu Gln Arg Trp Glu Glu Leu Met Arg Tyr Glu Arg Glu
    50                  55                  60

Leu Tyr Ala Ala Gly Val Arg Arg Ile Ala Gly Ile Asp Glu Ala Gly
65                  70                  75                  80

Arg Gly Pro Leu Ala Gly Pro Val Val Ala Ala Val Ile Leu Pro
                85                  90                  95

Lys Asp Ala Tyr Leu Pro Gly Leu Asp Asp Ser Lys Arg Leu Thr Pro
            100                 105                 110

Glu Lys Arg Glu Ala Leu Phe Ala Gln Ile Glu Ala Cys Ala Val Ala
        115                 120                 125

Ile Gly Ile Gly Ile Val Ser Ala Ala Glu Ile Asp Glu Arg Asn Ile
    130                 135                 140

Tyr Glu Ala Thr Arg Gln Ala Met Ala Lys Ala Val Asn Ala Leu Ser
145                 150                 155                 160

Pro Pro Pro Glu His Leu Leu Val Asp Ala Met Ala Val Pro Cys Pro
                165                 170                 175

Leu Pro Gln Gln Arg Leu Ile Lys Gly Asp Ala Asn Ser Ala Ser Ile
            180                 185                 190

Ala Ala Ala Ser Val Ile Ala Lys Val Thr Arg Asp Arg Trp Met Lys
        195                 200                 205

Glu Leu Asp Arg Arg Tyr Pro Gln Tyr Gly Phe Ala Arg His Met Gly
    210                 215                 220
```

Tyr Gly Thr Pro Glu His Phe Glu Ala Ile Arg Arg Tyr Gly Val Thr
225                 230                 235                 240

Pro Glu His Arg Arg Ser Phe Ala Pro Val Arg Glu Val Leu Lys Ala
            245                 250                 255

Ser Glu Gln Leu
        260

<210> SEQ ID NO 10
<211> LENGTH: 20
<212> TYPE: DNA
<213> ORGANISM: Artificial
<220> FEATURE:
<223> OTHER INFORMATION: PCR primer BsuIII-1 for cloning a gene encoding
      a polypeptide having a RNaseHIII activity from Bacillus caldotenax

<400> SEQUENCE: 10
ggtaaggtct tgttycargg                                                      20

<210> SEQ ID NO 11
<211> LENGTH: 20
<212> TYPE: DNA
<213> ORGANISM: Artificial
<220> FEATURE:
<223> OTHER INFORMATION: PCR primer BsuIII-3 for cloning a gene encoding
      a polypeptide having a RNaseHIII activity from Bacillus caldotenax

<400> SEQUENCE: 11
ggaaccggag attayttygg                                                      20

<210> SEQ ID NO 12
<211> LENGTH: 20
<212> TYPE: DNA
<213> ORGANISM: Artificial
<220> FEATURE:
<223> OTHER INFORMATION: PCR primer BsuIII-6 for cloning a gene encoding
      a polypeptide having a RNaseHIII activity from Bacillus caldotenax
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 12
atgattgaag cagcngcnac                                                      20

<210> SEQ ID NO 13
<211> LENGTH: 20
<212> TYPE: DNA
<213> ORGANISM: Artificial
<220> FEATURE:
<223> OTHER INFORMATION: PCR primer BsuIII-8 for cloning a gene encoding
      a polypeptide having a RNaseHIII activity from Bacillus caldotenax
<220> FEATURE:
<221> NAME/KEY: misc_feature
<222> LOCATION: (15)..(15)
<223> OTHER INFORMATION: n is a, c, g, or t

<400> SEQUENCE: 13
gtattggcga aatgnarytt                                                      20

<210> SEQ ID NO 14
<211> LENGTH: 20
<212> TYPE: DNA
<213> ORGANISM: Artificial
<220> FEATURE:

-continued

<223> OTHER INFORMATION: PCR primer RNIII-S3 for cloning a gene encoding
a polypeptide having a RNaseHIII activity from Bacillus caldotenax

<400> SEQUENCE: 14
cccgatcgtc gtcgccgccg                                              20

<210> SEQ ID NO 15
<211> LENGTH: 20
<212> TYPE: DNA
<213> ORGANISM: Artificial
<220> FEATURE:
<223> OTHER INFORMATION: PCR primer BcaRNIII-3 for cloning a gene
encoding a polypeptide having a RNaseHIII activity from
Bacillus caldotenax

<400> SEQUENCE: 15
gatacgtgga cactttccgc                                              20

<210> SEQ ID NO 16
<211> LENGTH: 915
<212> TYPE: DNA
<213> ORGANISM: Bacillus caldotenax

<400> SEQUENCE: 16
gtgattcaag ccgaccaaca gctgcttgac gccttgcgcg cccactacca agacgcctta      60
tccgaccggc ttccggctgg agcgttgttt gccgtcaagc gcccggatgt cgtcatcacc     120
gcctaccgct caggcaaagt gctgtttcaa gggaaagcgg cggagcaaga agcagcgaaa     180
tggatatcag gggcgagcgc ctcaaacgaa acagctgacc accagccgtc cgctttggca     240
gctcatcaac tcgggtctct ttccgccatc ggttccgatg aagtcggcac cggcgattat     300
ttcggcccga tcgtcgtcgc cgccgcctac gtggatcggc gcatatcgc caaaatcgcg     360 gcgcttggcg tgaaagattc gaaacaattg aacgatgagg caatcaaacg atcgcccccc     420
gccatcatgg aaaccgtgcc gcatgcggtc accgtgttgg acaatgccga atacaaccgc     480
tggcagcgaa gcggcatgcc gcagacgaaa atgaaagcgc tccttcacaa ccggacgctc     540
gtgaaactcg ttgacgccat cgcgcccgcc gaaccagaag caatcatcat cgacgaattt     600
ttaaaacggg attcgtattt ccgttaccct tccgatgaag atcgcattat ccgcgagcgg     660
gtgcactgcc ttcccaaggc ggaaagtgtc cacgtatcag tcgccgccgc ctcgatcatc     720
gcccgctatg tgtttttaga ggagatggag caattatccc gcgccgtcgg cctcctgctt     780
ccaaaaggcg ccggcgccat tgtcgatgaa gccgcggcca acatcatccg cgcgcggggg     840
gcggaagcgc ttgagacatg cgccaagctt catttcgcca atacaaaaaa ggcgctggac     900
atcgccaaac gccgg                                                      915

<210> SEQ ID NO 17
<211> LENGTH: 305
<212> TYPE: PRT
<213> ORGANISM: Bacillus caldotenax

<400> SEQUENCE: 17

Met Ile Gln Ala Asp Gln Gln Leu Leu Asp Ala Leu Arg Ala His Tyr
 1               5                  10                  15

Gln Asp Ala Leu Ser Asp Arg Leu Pro Ala Gly Ala Leu Phe Ala Val
             20                  25                  30

Lys Arg Pro Asp Val Val Ile Thr Ala Tyr Arg Ser Gly Lys Val Leu
         35                  40                  45

Phe Gln Gly Lys Ala Ala Glu Gln Glu Ala Ala Lys Trp Ile Ser Gly

```
                   50                  55                  60
Ala Ser Ala Ser Asn Glu Thr Ala Asp His Gln Pro Ser Ala Leu Ala
 65                  70                  75                  80

Ala His Gln Leu Gly Ser Leu Ser Ala Ile Gly Ser Asp Val Gly
                 85                  90                  95

Thr Gly Asp Tyr Phe Gly Pro Ile Val Val Ala Ala Tyr Val Asp
                100                 105                 110

Arg Pro His Ile Ala Lys Ile Ala Ala Leu Gly Val Lys Asp Ser Lys
                115                 120                 125

Gln Leu Asn Asp Glu Ala Ile Lys Arg Ile Ala Pro Ala Ile Met Glu
130                 135                 140

Thr Val Pro His Ala Val Thr Val Leu Asp Asn Ala Glu Tyr Asn Arg
145                 150                 155                 160

Trp Gln Arg Ser Gly Met Pro Gln Thr Lys Met Lys Ala Leu Leu His
                165                 170                 175

Asn Arg Thr Leu Val Lys Leu Val Asp Ala Ile Ala Pro Ala Glu Pro
                180                 185                 190

Glu Ala Ile Ile Ile Asp Glu Phe Leu Lys Arg Asp Ser Tyr Phe Arg
                195                 200                 205

Tyr Leu Ser Asp Glu Asp Arg Ile Ile Arg Glu Arg Val His Cys Leu
                210                 215                 220

Pro Lys Ala Glu Ser Val His Val Ser Val Ala Ala Ser Ile Ile
225                 230                 235                 240

Ala Arg Tyr Val Phe Leu Glu Glu Met Glu Gln Leu Ser Arg Ala Val
                245                 250                 255

Gly Leu Leu Leu Pro Lys Gly Ala Gly Ala Ile Val Asp Glu Ala Ala
                260                 265                 270

Ala Asn Ile Ile Arg Ala Arg Gly Ala Glu Leu Glu Thr Cys Ala
                275                 280                 285

Lys Leu His Phe Ala Asn Thr Lys Lys Ala Leu Asp Ile Ala Lys Arg
                290                 295                 300

Arg
305

<210> SEQ ID NO 18
<211> LENGTH: 39
<212> TYPE: DNA
<213> ORGANISM: Artificial
<220> FEATURE:
<223> OTHER INFORMATION: PCR primer BcaRNIIINde for amplifying a gene
      encoding a polypeptide having a RNaseHIII activity from Bacillus
      caldotenax

<400> SEQUENCE: 18
cgaacgttgt caaaccatat gattcaagcc gaccaacag                          39

<210> SEQ ID NO 19
<211> LENGTH: 663
<212> TYPE: DNA
<213> ORGANISM: Pyrococcus horikoshii

<400> SEQUENCE: 19
atgaaggttg ctggagttga tgaagcgggg aggggccgg taattggccc gttagtaatt     60
ggagtagccg ttatagatga gaaaaatatt gagaggttac gtgacattgg ggttaaagac    120
tccaaacaat taactcctgg gcaacgtgaa aaactattta gcaaattaat agatatccta    180
gacgattatt atgttcttct cgttaccccc aaggaaatag atgagaggca tcattctatg    240
```

-continued

```
aatgaactag aagctgagaa attcgttgta gccttgaatt ctttaaggat caagccgcag    300
aagatatatg tggactctgc cgatgtagat cctaagaggt ttgctagtct aataaaggct    360
gggttgaaat atgaagccac ggttatcgcc gagcataaag ccgatgcaaa gtatgagata    420
gtatcggcag catcaataat tgcaaaggtc actagggata gagagataga aagctaaag     480 caaaagtatg gggaatttgg ttctggctat ccgagtgatc cgagaactaa ggagtggctt    540
gaagaatatt acaaacaata tggtgacttt cctccaatag ttaggagaac ttgggaaacc    600
gctaggaaga tagaggaaag gtttagaaaa aatcagctaa cgcttgataa attccttaag    660
tga                                                                  663

<210> SEQ ID NO 20
<211> LENGTH: 33
<212> TYPE: DNA
<213> ORGANISM: Artificial
<220> FEATURE:
<223> OTHER INFORMATION: PCR primer 1650Nde for cloning a gene encoding
      a polypeptide having a RNaseHII activity from Pyrococcus furiosus

<400> SEQUENCE: 20
caggaggaga gacatatgaa aataggggga att                                 33

<210> SEQ ID NO 21
<211> LENGTH: 33
<212> TYPE: DNA
<213> ORGANISM: Artificial
<220> FEATURE:
<223> OTHER INFORMATION: PCR primer 1650Bam for cloning a gene encoding
      a polypeptide having a RNaseHII activity from Pyrococcus furiosus

<400> SEQUENCE: 21
gaaggttgtg gatccacttt ctaaggtttc tta                                 33

<210> SEQ ID NO 22
<211> LENGTH: 672
<212> TYPE: DNA
<213> ORGANISM: Pyrococcus furiosus

<400> SEQUENCE: 22
atgaaaatag ggggaattga cgaagcagga agaggaccag cgatagggcc attagtagta    60
gctactgtcg tcgttgatga gaaaaacatt gagaagctca gaaacattgg agtaaaagac    120
tccaaacaac taacacccca tgaaaggaag aatttatttt cccagataac ctcaatagcg    180
gatgattaca aaatagtgat agtatcccca gaagaaatcg acaatagatc aggaacaatg    240
aacgagttag aggtagagaa gtttgctctc gccttaaatt cgcttcagat aaaaccagct    300
cttatatacg ctgatgcagc ggatgtagat gccaatagat ttgcaagctt gatagagaga    360
agactcaatt ataaggcgaa gattattgcc gaacacaagg ccgatgcaaa gtatccagta    420
gtttcagcag cttcaatact tgcaaaggtt gttagggatg aggaaattga aaattaaaa    480 aagcaatatg gagactttgg ctctgggtat ccaagtgatc caaaaaccaa gaatggcttt   540
gaagagtact acaaaaaaca caactctttc cctccaatag tcagacgaac ctgggaaact   600
gtaagaaaaa tagaggaaag cattaaagcc aaaaaatccc agctaacgct tgataaattc   660
tttaagaaac ct                                                       672

<210> SEQ ID NO 23
<211> LENGTH: 224
<212> TYPE: PRT
```

<213> ORGANISM: Pyrococcus furiosus

<400> SEQUENCE: 23

```
Met Lys Ile Gly Gly Ile Asp Glu Ala Gly Arg Gly Pro Ala Ile Gly
1               5                   10                  15

Pro Leu Val Val Ala Thr Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
130                 135                 140

Ser Ile Leu Ala Lys Val Val Arg Asp Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220
```

<210> SEQ ID NO 24
<211> LENGTH: 28
<212> TYPE: DNA
<213> ORGANISM: Artificial
<220> FEATURE:
<223> OTHER INFORMATION: PCR primer 915-F1 for cloning a gene encoding
      a polypeptide having a RNaseHII activity from Thermotoga maritima

<400> SEQUENCE: 24
aaaaagcttg ggaatagatg agctttac                                    28

<210> SEQ ID NO 25
<211> LENGTH: 26
<212> TYPE: DNA
<213> ORGANISM: Artificial
<220> FEATURE:
<223> OTHER INFORMATION: PCR primer 915-F2 for cloning a gene encoding
      a polypeptide having a RNaseHII activity from Thermotoga maritima

<400> SEQUENCE: 25
aaaccatggg aatagatgag ctttac                                      26

<210> SEQ ID NO 26
<211> LENGTH: 29
<212> TYPE: DNA
<213> ORGANISM: Artificial
<220> FEATURE:
<223> OTHER INFORMATION: PCR primer 915-R1 for cloning a gene encoding a polypeptide having a RNaseHII activity from Thermotoga maritima

<400> SEQUENCE: 26
aaatctagat cctcaacttt gtcgatgtg                                   29

<210> SEQ ID NO 27
<211> LENGTH: 30
<212> TYPE: DNA
<213> ORGANISM: Artificial
<220> FEATURE:
<223> OTHER INFORMATION: PCR primer 915-R2 for cloning a gene encoding
      a polypeptide having a RNaseHII activity from Thermotoga maritima

<400> SEQUENCE: 27
aatctagatt aaaaaagagg gagattatgg                                  30

<210> SEQ ID NO 28
<211> LENGTH: 663
<212> TYPE: DNA
<213> ORGANISM: Pyrococcus horikoshii

<400> SEQUENCE: 28
atgaaggttg ctggagttga tgaagcgggg aggggccgg taattggccc gttagtaatt    60
ggagtagccg ttatagatga gaaaaatatt gagaggttac gtgacattgg ggttaaagac   120
tccaaacaat taactcctgg gcaacgtgaa aaactattta gcaaattaat agatatccta   180
gacgattatt atgttcttct cgttaccccc aaggaaatag atgagaggca tcattctatg   240
aatgaactag aagctgagaa attcgttgta gccttgaatt ctttaaggat caagccgcag   300
aagatatatg tggactctgc cgatgtagat cctaagaggt ttgctagtct aataaaggct   360
gggttgaaat atgaagccac ggttatcgcc gagcataaag ccgatgcaaa gtatgagata   420
gtatcggcag catcaataat tgcaaaggtc actagggata gagagataga gaagctaaag   480
caaaagtatg gggaatttgg ttctggctat ccgagtgatc cgagaactaa ggagtggctt   540
gaagaatatt acaaacaata tggtgacttt cctccaatag ttaggagaac ttgggaaacc   600
gctaggaaga tagaggaaag gtttagaaaa aatcagctaa cgcttgataa attccttaag   660
tga                                                               663

<210> SEQ ID NO 29
<211> LENGTH: 30
<212> TYPE: DNA
<213> ORGANISM: Artificial
<220> FEATURE:
<223> OTHER INFORMATION: PCR primer PhoNde for cloning a gene encoding
      a polypeptide having a RNaseHII activity from Pyrococcus
      horikoshii

<400> SEQUENCE: 29
aggaggaaaa tcatatgaag gttgctggag                                  30

<210> SEQ ID NO 30
<211> LENGTH: 30
<212> TYPE: DNA
<213> ORGANISM: Artificial
<220> FEATURE:
<223> OTHER INFORMATION: PCR primer PhoBam for cloning a gene encoding
      a polypeptide having a RNaseHII activity from Pyrococcus
      horikoshii

<400> SEQUENCE: 30
ttacatgaag gatccaagat cacttaagga                                  30

<210> SEQ ID NO 31
<211> LENGTH: 673
<212> TYPE: DNA
<213> ORGANISM: Pyrococcus horikoshii

<400> SEQUENCE: 31

```
atgaaggttg ctggagttga tgaagcgggg aggggccgg taattggccc gttagtaatt       60
ggagtagccg ttatagatga aaaaatatt gagaggttac gtgacattgg ggttaaagac      120
tccaaacaat taactcctgg caacgtgaa aaactattta gcaaattaat agatatccta      180
gacgattatt atgttcttct cgttaccccc aaggaaatag atgagaggca tcattctatg      240
aatgaactag aagctgagaa attcgttgta gccttgaatt ctttaaggat caagccgcag      300
aagatatatg tggactctgc cgatgtagat cctaagaggt ttgctagtct aataaaggct      360
gggttgaaat atgaagccac ggttatcgcc gagcataaag ccgatgcaaa gtatgagata      420
gtatcggcag catcaataat tgcaaaggtc actaggata gagagataga aagctaaag      480
caaaagtatg ggaatttgg ttctggctat ccgagtgatc cgagaactaa ggagtggctt      540
gaagaatatt acaaacaata tggtgacttt cctccaatag ttaggagaac ttgggaaacc      600
gctaggaaga tagaggaaag gtttagaaaa aatcagctaa cgcttgataa attccttaag      660
tgatcttgga tcc                                                        673
```

<210> SEQ ID NO 32
<211> LENGTH: 220
<212> TYPE: PRT
<213> ORGANISM: Pyrococcus horikoshii

<400> SEQUENCE: 32

```
Met Lys Val Ala Gly Val Asp Glu Ala Gly Arg Gly Pro Val Ile Gly
1               5                   10                  15

Pro Leu Val Ile Gly Val Ala Val Ile Asp Glu Lys Asn Ile Glu Arg
            20                  25                  30

Leu Arg Asp Ile Gly Val Lys Asp Ser Lys Gln Leu Thr Pro Gly Gln
        35                  40                  45

Arg Glu Lys Leu Phe Ser Lys Leu Ile Asp Ile Leu Asp Asp Tyr Tyr
    50                  55                  60

Val Leu Leu Val Thr Pro Lys Glu Ile Asp Glu Arg His His Ser Met
65                  70                  75                  80

Asn Glu Leu Glu Ala Glu Lys Phe Val Val Ala Leu Asn Ser Leu Arg
                85                  90                  95

Ile Lys Pro Gln Lys Ile Tyr Val Asp Ser Ala Asp Val Asp Pro Lys
            100                 105                 110

Arg Phe Ala Ser Leu Ile Lys Ala Gly Leu Lys Tyr Glu Ala Thr Val
        115                 120                 125

Ile Ala Glu His Lys Ala Asp Ala Lys Tyr Glu Ile Val Ser Ala Ala
    130                 135                 140

Ser Ile Ile Ala Lys Val Thr Arg Asp Arg Glu Ile Glu Lys Leu Lys
145                 150                 155                 160

Gln Lys Tyr Gly Glu Phe Gly Ser Gly Tyr Pro Ser Asp Pro Arg Thr
                165                 170                 175

Lys Glu Trp Leu Glu Glu Tyr Tyr Lys Gln Tyr Gly Asp Phe Pro Pro
            180                 185                 190

Ile Val Arg Arg Thr Trp Glu Thr Ala Arg Lys Ile Glu Glu Arg Phe
        195                 200                 205
```

-continued

```
Arg Lys Asn Gln Leu Thr Leu Asp Lys Phe Leu Lys
    210                 215                 220
```

<210> SEQ ID NO 33
<211> LENGTH: 626
<212> TYPE: DNA
<213> ORGANISM: Archaeoglobus fulgidus

<400> SEQUENCE: 33

```
atgaaggcag gcatcgatga ggctggaaag ggctgcgtca tcggcccact ggttgttgca      60
ggagtggctt gcagcgatga ggataggctg agaaagcttg gtgtgaaaga ctccaaaaag     120
ctaagtcagg ggaggagaga ggaactagcc gaggaaataa ggaaaatctg cagaacggag     180
gttttgaaag tttctcccga aaatctcgac gaaaggatgg ctgctaaaac cataaacgag     240
attttgaagg agtgctacgc tgaaataatt ctcaggctga agccggaaat tgcttatgtt     300
gacagtcctg atgtgattcc cgagagactt tcgagggagc ttgaggagat tacggggttg     360
agagttgtgg ccgagcacaa ggcggacgag aagtatcccc tggtagctgc ggcttcaatc     420
atcgcaaagg tggaaaggga gcgggagatt gagaggctga agaaaaaatt cggggatttc     480
ggcagcggct atgcgagcga tccgaggaca agagaagtgc tgaaggagtg gatagcttca     540
ggcagaattc cgagctgcgt gagaatgcgc tggaagacgg tgtcaaatct gaggcagaag     600
acgcttgacg atttctaaac gaaacc                                          626
```

<210> SEQ ID NO 34
<211> LENGTH: 30
<212> TYPE: DNA
<213> ORGANISM: Artificial
<220> FEATURE:
<223> OTHER INFORMATION: PCR primer AfuNde for cloning a gene encoding a polypeptide having a RNaseHII activity from Archaeoglobus fulgidus

<400> SEQUENCE: 34

```
aagctgggtt tcatatgaag gcaggcatcg                                       30
```

<210> SEQ ID NO 35
<211> LENGTH: 30
<212> TYPE: DNA
<213> ORGANISM: Artificial
<220> FEATURE:
<223> OTHER INFORMATION: PCR primer AfuBam for cloning a gene encoding a polypeptide having a RNaseHII activity from Archaeoglobus fulgidus

<400> SEQUENCE: 35

```
tggtaataac ggatccgttt agaaatcgtc                                       30
```

<210> SEQ ID NO 36
<211> LENGTH: 638
<212> TYPE: DNA
<213> ORGANISM: Archaeoglobus fulgidus

<400> SEQUENCE: 36

```
catatgaagg caggcatcga tgaggctgga aagggctgcg tcatcggccc actggttgtt      60
gcaggagtgg cttgcagcga tgaggatagg ctgagaaagc ttggtgtgaa agactccaaa     120
aagctaagtc aggggaggag agaggaacta gccgaggaaa taggaaaaat ctgcagaacg     180
gaggttttga agtttctccc gaaaatctc gacgaaagga tggctgctaa aaccataaac     240
gagattttga aggagtgcta cgctgaaata attctcaggc tgaagccgga aattgcttat     300
```

-continued

```
gttgacagtc ctgatgtgat tcccgagaga cttccgaggg agcttgagga gattacgggg    360
ttgagagttg tggccgagca caaggcggac gagaagtatc ccctggtagc tgcggcttca    420
atcatcgcaa aggtggaaag ggagcggagg attgagaggc tgaaagaaaa attcggggat    480
ttcggcagcg gctatgcgag cgatccgagg acaagagaag tgctgaagga gtggatagct    540
tcaggcagaa ttccgagctg cgtgagaatg cgctggaaga cggtgtcaaa tctgaggcag    600
aagacgcttg acgatttcta aacggatccc cgggtacc                            638
```

<210> SEQ ID NO 37
<211> LENGTH: 205
<212> TYPE: PRT
<213> ORGANISM: Archaeoglobus fulgidus

<400> SEQUENCE: 37

```
Met Lys Ala Gly Ile Asp Glu Ala Gly Lys Gly Cys Val Ile Gly Pro
1               5                   10                  15

Leu Val Val Ala Gly Val Ala Cys Ser Asp Glu Asp Arg Leu Arg Lys
            20                  25                  30

Leu Gly Val Lys Asp Ser Lys Lys Leu Ser Gln Gly Arg Arg Glu Glu
        35                  40                  45

Leu Ala Glu Glu Ile Arg Lys Ile Cys Arg Thr Glu Val Leu Lys Val
    50                  55                  60

Ser Pro Glu Asn Leu Asp Glu Arg Met Ala Ala Lys Thr Ile Asn Glu
65                  70                  75                  80

Ile Leu Lys Glu Cys Tyr Ala Glu Ile Ile Leu Arg Leu Lys Pro Glu
                85                  90                  95

Ile Ala Tyr Val Asp Ser Pro Asp Val Ile Pro Glu Arg Leu Ser Arg
            100                 105                 110

Glu Leu Glu Glu Ile Thr Gly Leu Arg Val Val Ala Glu His Lys Ala
        115                 120                 125

Asp Glu Lys Tyr Pro Leu Val Ala Ala Ala Ser Ile Ile Ala Lys Val
    130                 135                 140

Glu Arg Glu Arg Glu Ile Glu Arg Leu Lys Glu Lys Phe Gly Asp Phe
145                 150                 155                 160

Gly Ser Gly Tyr Ala Ser Asp Pro Arg Thr Arg Glu Val Leu Lys Glu
                165                 170                 175

Trp Ile Ala Ser Gly Arg Ile Pro Ser Cys Val Arg Met Arg Trp Lys
            180                 185                 190

Thr Val Ser Asn Leu Arg Gln Lys Thr Leu Asp Asp Phe
        195                 200                 205
```

<210> SEQ ID NO 38
<211> LENGTH: 23
<212> TYPE: DNA
<213> ORGANISM: Artificial
<220> FEATURE:
<223> OTHER INFORMATION: PCR primer RN-F1 for cloning a gene encoding a
      polypeptide having a RNaseHII activity from Thermococcus
      litoralis
<220> FEATURE:
<221> NAME/KEY: misc_feature
<222> LOCATION: (18)..(18)
<223> OTHER INFORMATION: n is a, c, g, or t

<400> SEQUENCE: 38

```
ggcattgatg aggctggnar rgg                                             23
```

<210> SEQ ID NO 39

```
<211> LENGTH: 23
<212> TYPE: DNA
<213> ORGANISM: Artificial
<220> FEATURE:
<223> OTHER INFORMATION: PCR primer RN-R0 for cloning a gene encoding a
      polypeptide having a RNaseHII activity from Thermococcus
      litoralis
<220> FEATURE:
<221> NAME/KEY: misc_feature
<222> LOCATION: (21)..(21)
<223> OTHER INFORMATION: n is a, c, g, or t

<400> SEQUENCE: 39
gtccttggat cgctgggrta ncc                                            23

<210> SEQ ID NO 40
<211> LENGTH: 24
<212> TYPE: DNA
<213> ORGANISM: Artificial
<220> FEATURE:
<223> OTHER INFORMATION: PCR primer TliRN-1 for cloning a gene encoding
      a polypeptide having a RNaseHII activity from Thermococcus
      litoralis

<400> SEQUENCE: 40 tagcttttttt gaatctttga ctcc                                          24

<210> SEQ ID NO 41
<211> LENGTH: 24
<212> TYPE: DNA
<213> ORGANISM: Artificial
<220> FEATURE:
<223> OTHER INFORMATION: PCR primer TliRN-2 for cloning a gene encoding
      a polypeptide having a RNaseHII activity from Thermococcus
      litoralis

<400> SEQUENCE: 41
ctgctgcatc aatactagct aaag                                           24

<210> SEQ ID NO 42
<211> LENGTH: 675
<212> TYPE: DNA
<213> ORGANISM: Thermococcus litoralis

<400> SEQUENCE: 42
atgaagctgg gaggaataga tgaagccggc aggggaccag ttataggccc tcttgtaatt     60
gcagcggttg ttgtcgatga atcccgtatg caggagcttg aagctttggg agtcaaagat    120
tcaaaaaagc taacaccaaa aagaagagaa gagctatttg aggagattgt gcaaatagtt    180
gatgaccacg ttatcattca gctttcccca gaggagatag acggcagaga tggtacaatg    240
aacgagcttg aaattgaaaa cttttgccaaa gcgttgaact cccttaaagt taagccggat    300
gtgctctaca tagatgcggc cgatgtcaag gaaaagcgct ttggcgacat tataggtgaa    360
agactttcct tctctccaaa gataatcgcc gaacataagg cagattcaaa gtacattcca    420
gtggctgctg catcaatact agctaaagtt acccgtgaca gggcaataga gaagctcaag    480
gagctttatg gggagatagg ctcaggatat ccaagtgatc caaatacaag gaggtttctg    540
gaggagtatt acaaggctca tggggaattc cccccaatag tgaggaaaag ctggaagacc    600
cttagaaaga tagaagaaaa actaaaagct aaaagactc agcccactat cttggacttc    660
ttaaaaaagc cttaa                                                     675

<210> SEQ ID NO 43
<211> LENGTH: 224
```

```
<212> TYPE: PRT
<213> ORGANISM: Thermococcus litoralis

<400> SEQUENCE: 43

Met Lys Leu Gly Gly Ile Asp Glu Ala Gly Arg Gly Pro Val Ile Gly
1               5                   10                  15

Pro Leu Val Ile Ala Ala Val Val Asp Glu Ser Arg Met Gln Glu
            20                  25                  30

Leu Glu Ala Leu Gly Val Lys Asp Ser Lys Lys Leu Thr Pro Lys Arg
        35                  40                  45

Arg Glu Glu Leu Phe Glu Ile Val Gln Ile Val Asp Asp His Val
    50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
            100                 105                 110

Arg Phe Gly Asp Ile Ile Gly Glu Arg Leu Ser Phe Ser Pro Lys Ile
        115                 120                 125

Ile Ala Glu His Lys Ala Asp Ser Lys Tyr Ile Pro Val Ala Ala Ala
    130                 135                 140

Ser Ile Leu Ala Lys Val Thr Arg Asp Arg Ala Ile Glu Lys Leu Lys
145                 150                 155                 160

Glu Leu Tyr Gly Glu Ile Gly Ser Gly Tyr Pro Ser Asp Pro Asn Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
        195                 200                 205

Lys Ala Lys Lys Thr Gln Pro Thr Ile Leu Asp Phe Leu Lys Lys Pro
    210                 215                 220

<210> SEQ ID NO 44
<211> LENGTH: 39
<212> TYPE: DNA
<213> ORGANISM: Artificial
<220> FEATURE:
<223> OTHER INFORMATION: PCR primer TliNde for amplifying a gene
      encoding
      a polypeptide having a RNaseHII activity from Thermococcus
      litoralis

<400> SEQUENCE: 44
gaggaggtag gcatatgaag ctgggaggaa tagatgaag                              39

<210> SEQ ID NO 45
<211> LENGTH: 39
<212> TYPE: DNA
<213> ORGANISM: Artificial
<220> FEATURE:
<223> OTHER INFORMATION: PCR primer TliBam for amplifying a gene
      encoding
      a polypeptide having a RNaseHIII activity from Thermococcus
      litoralis

<400> SEQUENCE: 45
aaaggaaacc ttcggatcca ttaaggcttt tttaagaag                              39

<210> SEQ ID NO 46
```

<211> LENGTH: 675
<212> TYPE: DNA
<213> ORGANISM: Thermococcus litoralis

<400> SEQUENCE: 46

```
atgaagctgg gaggaataga tgaagccggc aggggaccag ttataggccc tcttgtaatt    60
gcagcggttg ttgtcgatga atcccgtatg caggagcttg aagctttggg agtcaaagat   120
tcaaaaaagc taacaccaaa agaagagaaa gagctatttg aggagattgt gcaaatagtt   180
gatgaccacg ttatcattca gctttcccca gaggagatag acggcagaga tggtacaatg   240
aacgagcttg aaattgaaaa ctttgccaaa gcgttgaact cccttaaagt taagccggat   300
gtgctctaca tagatgcggc cgatgtcaag gaaaagcgct ttggcgacat tataggtgaa   360
agactttcct ctctcccaaa gataatcgcc gaacataagg cagattcaaa gtacattcca   420
gtggctgctg catcaatact agctaaagtt acccgtgaca gggcaataga gaagctcaag   480
gagttttatg gggagatagg ctcaggatat ccaagtgatc caattacaag gaggtttctg   540
gaggagtatt acaaggctca tggggaattc cccccaatag tgaggaaaag ctggaagacc   600
cttagaaaga tagaagaaaa actaaaagct aaaaagactc agcccactat cttggacttc   660
ttaaaaaagc cttaa                                                    675
```

<210> SEQ ID NO 47
<211> LENGTH: 224
<212> TYPE: PRT
<213> ORGANISM: Thermococcus litoralis

<400> SEQUENCE: 47

```
Met Lys Leu Gly Gly Ile Asp Glu Ala Gly Arg Gly Pro Val Ile Gly
1               5                   10                  15

Pro Leu Val Ile Ala Ala Val Val Val Asp Glu Ser Arg Met Gln Glu
            20                  25                  30

Leu Glu Ala Leu Gly Val Lys Asp Ser Lys Lys Leu Thr Pro Lys Arg
        35                  40                  45

Arg Glu Glu Leu Phe Glu Glu Ile Val Gln Ile Val Asp Asp His Val
    50                  55                  60

Ile Ile Gln Leu Ser Pro Glu Glu Ile Asp Gly Arg Asp Gly Thr Met
65                  70                  75                  80

Asn Glu Leu Glu Ile Glu Asn Phe Ala Lys Ala Leu Asn Ser Leu Lys
                85                  90                  95

Val Lys Pro Asp Val Leu Tyr Ile Asp Ala Ala Asp Val Lys Glu Lys
            100                 105                 110

Arg Phe Gly Asp Ile Ile Gly Glu Arg Leu Ser Phe Ser Pro Lys Ile
        115                 120                 125

Ile Ala Glu His Lys Ala Asp Ser Lys Tyr Ile Pro Val Ala Ala Ala
    130                 135                 140

Ser Ile Leu Ala Lys Val Thr Arg Asp Arg Ala Ile Glu Lys Leu Lys
145                 150                 155                 160

Glu Phe Tyr Gly Glu Ile Gly Ser Gly Tyr Pro Ser Asp Pro Ile Thr
                165                 170                 175

Arg Arg Phe Leu Glu Glu Tyr Tyr Lys Ala His Gly Glu Phe Pro Pro
            180                 185                 190

Ile Val Arg Lys Ser Trp Lys Thr Leu Arg Lys Ile Glu Glu Lys Leu
        195                 200                 205

Lys Ala Lys Lys Thr Gln Pro Thr Ile Leu Asp Phe Leu Lys Lys Pro
    210                 215                 220
```

<210> SEQ ID NO 48
<211> LENGTH: 23
<212> TYPE: DNA
<213> ORGANISM: Artificial
<220> FEATURE:
<223> OTHER INFORMATION: PCR primer RN-F1 for cloning a gene encoding
      a polypeptide having a RNaseHII activity from Thermococcus celer
<220> FEATURE:
<221> NAME/KEY: misc_feature
<222> LOCATION: (18)..(18)
<223> OTHER INFORMATION: n is a, c, g, or t

<400> SEQUENCE: 48
ggcattgatg aggctggnar rgg                                            23

<210> SEQ ID NO 49
<211> LENGTH: 23
<212> TYPE: DNA
<213> ORGANISM: Artificial
<220> FEATURE:
<223> OTHER INFORMATION: PCR primer RN-R0 for cloning a gene encoding
      a polypeptide having a RNaseHII activity from Thermococcus celer
<220> FEATURE:
<221> NAME/KEY: misc_feature
<222> LOCATION: (21)..(21)
<223> OTHER INFORMATION: n is a, c, g, or t

<400> SEQUENCE: 49
gtccttggat cgctgggrta ncc                                            23

<210> SEQ ID NO 50
<211> LENGTH: 24
<212> TYPE: DNA
<213> ORGANISM: Artificial
<220> FEATURE:
<223> OTHER INFORMATION: PCR primer TceRN-1 for cloning a gene encoding
      a polypeptide having a RNaseHII activity from Thermococcus celer

<400> SEQUENCE: 50
tctctgagct tcggaacgtt cttc                                           24

<210> SEQ ID NO 51
<211> LENGTH: 24
<212> TYPE: DNA
<213> ORGANISM: Artificial
<220> FEATURE:
<223> OTHER INFORMATION: PCR primer TceRN-2 for cloning a gene encoding
      a polypeptide having a RNaseHII activity from Thermococcus celer

<400> SEQUENCE: 51
acccgtgaca gggcgataga aaag                                           24

<210> SEQ ID NO 52
<211> LENGTH: 702
<212> TYPE: DNA
<213> ORGANISM: Thermococcus celer

<400> SEQUENCE: 52
ttgaagctcg caggaataga cgaggctgga aggggccccg taatcggccc gatggtcatc      60
gcggccgtcg tcctcgatga agaacgtt ccgaagctca gagatctcgg cgtcagggac       120
tcgaaaaagc tgaccccaaa gaggagggag agattattta acgacataat taaacttttg    180
gatgattatg taattcttga attatggccg gaggagatag actcccgcgg cgggacgctt    240
aacgagctcg aggtggagag gttcgtggag gccctcaact cgcttaaggt gaagcccgac    300

```
gtcgtttaca tagacgcggc ggacgtgaag gagggccgct ttggcgagga gataaaggaa    360
aggttgaact tcgaggcgaa gattgtctca gagcacaggg cggacgataa gttttttaccg   420 gtgtcctctg cctcgatact ggcgaaggtg acccgtgaca gggcgataga aaagctcaag    480
gagaagtacg cgagatcgg gagcggctac ccgagcgacc caaggacgag ggagttcctc    540
gagaactact acagacaaca cggcgagttc ccgcccgtag tccggcgaag ctggaagacg    600
ctgagaaaga tagaggaaaa gctgaggaaa gaggccgggt caaaaaaccc ggagaattca    660
aaggaaaagg gacagacgag cctggacgta ttttgaggt ag                         702
```

<210> SEQ ID NO 53
<211> LENGTH: 233
<212> TYPE: PRT
<213> ORGANISM: Thermococcus celer

<400> SEQUENCE: 53

```
Leu Lys Leu Ala Gly Ile Asp Glu Ala Gly Arg Gly Pro Val Ile Gly
1               5                   10                  15

Pro Met Val Ile Ala Ala Val Val Leu Asp Glu Lys Asn Val Pro Lys
            20                  25                  30

Leu Arg Asp Leu Gly Val Arg Asp Ser Lys Lys Leu Thr Pro Lys Arg
        35                  40                  45

Arg Glu Arg Leu Phe Asn Asp Ile Ile Lys Leu Asp Asp Tyr Val
    50                  55                  60

Ile Leu Glu Leu Trp Pro Glu Glu Ile Asp Ser Arg Gly Gly Thr Leu
65                  70                  75                  80

Asn Glu Leu Glu Val Glu Arg Phe Val Glu Ala Leu Asn Ser Leu Lys
                85                  90                  95

Val Lys Pro Asp Val Val Tyr Ile Asp Ala Ala Asp Val Lys Glu Gly
            100                 105                 110

Arg Phe Gly Glu Glu Ile Lys Glu Arg Leu Asn Phe Glu Ala Lys Ile
        115                 120                 125

Val Ser Glu His Arg Ala Asp Asp Lys Phe Leu Pro Val Ser Ser Ala
    130                 135                 140

Ser Ile Leu Ala Lys Val Thr Arg Asp Arg Ala Ile Glu Lys Leu Lys
145                 150                 155                 160

Glu Lys Tyr Gly Glu Ile Gly Ser Gly Tyr Pro Ser Asp Pro Arg Thr
                165                 170                 175

Arg Glu Phe Leu Glu Asn Tyr Tyr Arg Gln His Gly Glu Phe Pro Pro
            180                 185                 190

Val Val Arg Arg Ser Trp Lys Thr Leu Arg Lys Ile Glu Glu Lys Leu
        195                 200                 205

Arg Lys Glu Ala Gly Ser Lys Asn Pro Glu Asn Ser Lys Glu Lys Gly
    210                 215                 220

Gln Thr Ser Leu Asp Val Phe Leu Arg
225                 230
```

<210> SEQ ID NO 54
<211> LENGTH: 39
<212> TYPE: DNA
<213> ORGANISM: Artificial
<220> FEATURE:
<223> OTHER INFORMATION: PCR primer TceNde for amplifying a gene
      encoding a polypeptide having a RNaseHII activity from
      Thermococcus celer

<400> SEQUENCE: 54
cagggggtga gcatatgaag ctcgcaggaa tagacgagg         39

<210> SEQ ID NO 55
<211> LENGTH: 39
<212> TYPE: DNA
<213> ORGANISM: Artificial
<220> FEATURE:
<223> OTHER INFORMATION: PCR primer TceBam for amplifying a gene
      encoding a polypeptide having a RNaseHII activity from
      Thermococcus celer

<400> SEQUENCE: 55
tgaacccgcg taggatccta cctcaaaaat acgtccagg         39

<210> SEQ ID NO 56
<211> LENGTH: 702
<212> TYPE: DNA
<213> ORGANISM: Thermococcus celer

<400> SEQUENCE: 56
atgaagctcg cagaaataga cgaggctgga aggggccccg taatcggccc gatggtcatc    60
gcggccgtcg tcctcgatga aaagaacgtt ccgaagctca gagatctcgg cgtcagggac   120
tcgaaaaagc tgaccccaaa gaggagggag agattattta cgacataat taaacttttg   180
gatgattatg taattcttga attatggccg gaggagatag actcccgcgg cgggacgctt   240
aacgagctcg aggtggagag gttcgtggag gccctcaact cgcttaaggt gaagcccgac   300
gtcgtttaca tagacgcggc ggacgtgaag gagggccgct ttggcgagga gataaaggaa   360
aggttgaact tcgaggcgaa gattgtctca gagcacaggg cggacgataa gttttttaccg   420
gtgtcctctg cctcgatact ggcgaaggtg acccgtgaca gggcgataga aaagctcaag   480
gagaagtacg gcgagatcgg gagcggctac ccgagcgacc caaggacgag ggagttcctc   540
gagaactact acagacaaca cggcgagttc ccgcccgtag tccggcgaag ctggaagacg   600
ctgagaaaga tagaggaaaa gctgaggaaa gaggccgggt caaaaaaccc ggagaattca   660
aaggaaaagg gacagacgag cctggacgta ttttttgaggt ag                     702

<210> SEQ ID NO 57
<211> LENGTH: 233
<212> TYPE: PRT
<213> ORGANISM: Thermococcus celer

<400> SEQUENCE: 57

Met Lys Leu Ala Glu Ile Asp Glu Ala Gly Arg Gly Pro Val Ile Gly
1               5                   10                  15

Pro Met Val Ile Ala Ala Val Val Leu Asp Glu Lys Asn Val Pro Lys
            20                  25                  30

Leu Arg Asp Leu Gly Val Arg Asp Ser Lys Lys Leu Thr Pro Lys Arg
        35                  40                  45

Arg Glu Arg Leu Phe Asn Asp Ile Ile Lys Leu Leu Asp Asp Tyr Val
    50                  55                  60

Ile Leu Glu Leu Trp Pro Glu Glu Ile Asp Ser Arg Gly Gly Thr Leu
65                  70                  75                  80

Asn Glu Leu Glu Val Glu Arg Phe Val Glu Ala Leu Asn Ser Leu Lys
                85                  90                  95

Val Lys Pro Asp Val Val Tyr Ile Asp Ala Ala Asp Val Lys Glu Gly
            100                 105                 110

Arg Phe Gly Glu Glu Ile Lys Glu Arg Leu Asn Phe Glu Ala Lys Ile
        115                 120                 125

-continued

Val Ser Glu His Arg Ala Asp Asp Lys Phe Leu Pro Val Ser Ser Ala
    130                 135                 140

Ser Ile Leu Ala Lys Val Thr Arg Asp Arg Ala Ile Glu Lys Leu Lys
145                 150                 155                 160

Glu Lys Tyr Gly Glu Ile Gly Ser Gly Tyr Pro Ser Asp Pro Arg Thr
            165                 170                 175

Arg Glu Phe Leu Glu Asn Tyr Tyr Arg Gln His Gly Glu Phe Pro Pro
        180                 185                 190

Val Val Arg Arg Ser Trp Lys Thr Leu Arg Lys Ile Glu Glu Lys Leu
    195                 200                 205

Arg Lys Glu Ala Gly Ser Lys Asn Pro Glu Asn Ser Lys Glu Lys Gly
210                 215                 220

Gln Thr Ser Leu Asp Val Phe Leu Arg
225                 230

<210> SEQ ID NO 58
<211> LENGTH: 714
<212> TYPE: DNA
<213> ORGANISM: Thermotoga maritime

<400> SEQUENCE: 58
atgggaatag atgagcttta caaaaaagag tttggaatcg tagcaggtgt ggatgaagcg    60
ggaagagggt gcctcgcagg tcccgttgtg gcggccgctg tcgttctgga aaagaaata   120 gaaggaataa acgattcaaa acagctttcc cctgcgaaga gggaaagact tttagatgaa   180
ataatggaga aggcagcagt tgggttagga attgcgtctc cagaggaaat agatctctac   240
aacatattca atgccacaaa acttgctatg aatcgagcac tggagaacct gtctgtgaaa   300
ccatcatttg tactcgttga cgggaaagga atcgagttga gcgttcccgg tacatgctta   360
gtgaagggag accagaaaag caaattgata ggagcagctt ccattgttgc aaggtcttc    420 agagatagat tgatgagcga gttttcacagg atgtatccac agttttcctt ccacaaacac   480
aaaggttacg ccacaaaaga acatctgaac gaaatcagaa agaacggagt tttaccaatc   540
caccggctga gttttgaacc tgtttttagaa cttctgaccg atgatttgtt gagggagttc   600
ttcgaaaaag gcctcatctc cgaaaatcga ttcgaacgaa tattgaatct tctgggggcg   660
agaaaaagtg tggttttccg gaagaaaga acaaaccata atctccctct tttt           714

<210> SEQ ID NO 59
<211> LENGTH: 238
<212> TYPE: PRT
<213> ORGANISM: Thermotoga maritime

<400> SEQUENCE: 59

Met Gly Ile Asp Glu Leu Tyr Lys Lys Glu Phe Gly Ile Val Ala Gly
1               5                   10                  15

Val Asp Glu Ala Gly Arg Gly Cys Leu Ala Gly Pro Val Val Ala Ala
            20                  25                  30

Ala Val Val Leu Glu Lys Glu Ile Glu Gly Ile Asn Asp Ser Lys Gln
        35                  40                  45

Leu Ser Pro Ala Lys Arg Glu Arg Leu Leu Asp Glu Ile Met Glu Lys
    50                  55                  60

Ala Ala Val Gly Leu Gly Ile Ala Ser Pro Glu Glu Ile Asp Leu Tyr
65                  70                  75                  80

Asn Ile Phe Asn Ala Thr Lys Leu Ala Met Asn Arg Ala Leu Glu Asn
                85                  90                  95

Leu Ser Val Lys Pro Ser Phe Val Leu Val Asp Gly Lys Gly Ile Glu
            100                 105                 110

Leu Ser Val Pro Gly Thr Cys Leu Val Lys Gly Asp Gln Lys Ser Lys
            115                 120                 125

Leu Ile Gly Ala Ala Ser Ile Val Ala Lys Val Phe Arg Asp Arg Leu
        130                 135                 140

Met Ser Glu Phe His Arg Met Tyr Pro Gln Phe Ser Phe His Lys His
145                 150                 155                 160

Lys Gly Tyr Ala Thr Lys Glu His Leu Asn Glu Ile Arg Lys Asn Gly
                165                 170                 175

Val Leu Pro Ile His Arg Leu Ser Phe Glu Pro Val Leu Glu Leu Leu
            180                 185                 190

Thr Asp Asp Leu Leu Arg Glu Phe Phe Lys Gly Leu Ile Ser Glu
            195                 200                 205

Asn Arg Phe Glu Arg Ile Leu Asn Leu Leu Gly Ala Arg Lys Ser Val
        210                 215                 220

Val Phe Arg Lys Glu Arg Thr Asn His Asn Leu Pro Leu Phe
225                 230                 235

<210> SEQ ID NO 60
<211> LENGTH: 17
<212> TYPE: DNA
<213> ORGANISM: Artificial
<220> FEATURE:
<223> OTHER INFORMATION: Designed oligonucleotide as tag sequence.

<400> SEQUENCE: 60
ggcacgattc gataacg                                                  17

<210> SEQ ID NO 61
<211> LENGTH: 20
<212> TYPE: DNA
<213> ORGANISM: Artificial
<220> FEATURE:
<223> OTHER INFORMATION: Designed chimeric oligonucleotide primer as
      VT2-R280N3-I7 for
      amplifying a portion of vero toxin 2-encoding sequence from
      hemorrhagic Escherichia coli O-157."Nucleotides 18 to 20 are
      ribonucleotides-other nucleotides are deoxyribonucleotides"
<220> FEATURE:
<221> NAME/KEY: misc_feature
<222> LOCATION: (14)..(14)
<223> OTHER INFORMATION: n is a, c, g, or t

<400> SEQUENCE: 61
tgctcaataa tcanacgaag                                               20

<210> SEQ ID NO 62
<211> LENGTH: 22
<212> TYPE: DNA
<213> ORGANISM: Artificial
<220> FEATURE:
<223> OTHER INFORMATION: Designed oligonucleotide primer as VT2-F110
      for amplifying a portion of vero toxin 2-encoding sequence from
      hemorrhagic Escherichia coli O-157.

<400> SEQUENCE: 62
tcgttaaata gtatacggga ag                                            22

<210> SEQ ID NO 63
<211> LENGTH: 19
<212> TYPE: DNA
<213> ORGANISM: Artificial

-continued

```
<220> FEATURE:
<223> OTHER INFORMATION: Designed chimeric oligonucleotide primer as
      VT2-IF20N3 for
      amplifying a VFN3 from hemorrhagic Escherichia coli
      O-157."Nucleotides 17 to 19 are ribonucleotides-other nucleotides
      are deoxyribonucleotides"

<400> SEQUENCE: 63
tactgggttt ttcttcgua                                                    19

<210> SEQ ID NO 64
<211> LENGTH: 18
<212> TYPE: DNA
<213> ORGANISM: Artificial
<220> FEATURE:
<223> OTHER INFORMATION: Designed chimeric oligonucleotide primer as
      VT2-IF19N2 for
      amplifying VFN2 from hemorrhagic Escherichia coli
      O-157."Nucleotides 16 to 18 are ribonucleotides-other nucleotides
      are deoxyribonucleotides"

<400> SEQUENCE: 64
tactgggttt ttcttcgu                                                     18

<210> SEQ ID NO 65
<211> LENGTH: 17
<212> TYPE: DNA
<213> ORGANISM: Artificial
<220> FEATURE:
<223> OTHER INFORMATION: Designed chimeric oligonucleotide primer as
      VT2-IF18N1 for
      amplifying a VFN1 from hemorrhagic Escherichia coli
      O-157."Nucleotides 15 to 17 are ribonucleotides-other nucleotides
      are deoxyribonucleotides"

<400> SEQUENCE: 65
tactgggttt ttcttcg                                                      17

<210> SEQ ID NO 66
<211> LENGTH: 20
<212> TYPE: DNA
<213> ORGANISM: Artificial
<220> FEATURE:
<223> OTHER INFORMATION: Designed oligonucleotide primer as VT21R20
      for amplifying a
      portion of vero toxin 2-encoding sequence from hemorrhagic
      Escherichia coli O-157.

<400> SEQUENCE: 66
gtcccctgag atatatgttc                                                   20
```